United States Patent [19]

Nakagawa et al.

[11] 4,216,220
[45] Aug. 5, 1980

[54] PLATELET AGGREGATION INHIBITING 2-OXYINDOLES, THEIR COMPOSITIONS AND METHOD OF USE

[75] Inventors: Kazuyuki Nakagawa, Tokushima; Minoru Uchida, Komatsushima; Kimiaki Oka, Tokushima, all of Japan

[73] Assignee: Otsuka Pharmaceutical Co., Ltd., Japan

[21] Appl. No.: 806,926

[22] Filed: Jun. 15, 1977

Related U.S. Application Data

[62] Division of Ser. No. 588,475, Jun. 19, 1975, Pat. No. 4,070,470.

[30] Foreign Application Priority Data

| Jun. 24, 1974 | [JP] | Japan | 49-72472 |
|---|---|---|---|
| Jun. 24, 1974 | [JP] | Japan | 49-72473 |
| Jul. 5, 1974 | [JP] | Japan | 49-77660 |
| Jul. 5, 1974 | [JP] | Japan | 49-77661 |
| Aug. 16, 1974 | [JP] | Japan | 49-94376 |
| Apr. 30, 1975 | [JP] | Japan | 50-53026 |
| Apr. 30, 1975 | [JP] | Japan | 50-53027 |
| Apr. 30, 1975 | [JP] | Japan | 50-53028 |
| May 15, 1975 | [JP] | Japan | 50-58127 |
| May 15, 1975 | [JP] | Japan | 50-58128 |
| May 15, 1975 | [JP] | Japan | 50-58129 |
| May 15, 1975 | [JP] | Japan | 50-58134 |
| May 15, 1975 | [JP] | Japan | 50-58135 |
| May 16, 1975 | [JP] | Japan | 50-58872 |
| May 16, 1975 | [JP] | Japan | 50-58874 |
| Jun. 2, 1975 | [JP] | Japan | 50-66729 |

[51] Int. Cl.$^2$ .................................... C07D 209/04
[52] U.S. Cl. .................... 424/274; 260/326.11 R; 260/326.13 R
[58] Field of Search ...... 260/268 H, 302 H, 326.13 R, 260/326.11 R; 424/274

[56] References Cited

U.S. PATENT DOCUMENTS

| 3,340,266 | 9/1967 | Howe et al. | 260/288 CF |
|---|---|---|---|
| 3,509,163 | 4/1970 | Brandstrom et al. | 260/326.13 R |
| 3,514,459 | 5/1970 | Ritter et al. | 260/287 K |
| 3,749,731 | 7/1973 | Zinnes et al. | 260/306.8 R |
| 3,919,239 | 11/1975 | Naragana et al. | 260/287 K |

Primary Examiner—Nicholas S. Rizzo
Attorney, Agent, or Firm—Finnegan, Henderson, Farabow, Garrett & Dunner

[57] ABSTRACT

2-Oxyindole derivatives represented by the following general formula:

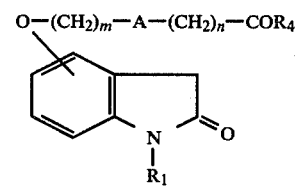

where $R_1$ is selected from the group consisting of hydrogen, $C_{1-4}$ alkyl, $C_{2-4}$ alkenyl, benzyl and phenethyl; A is —CH=CH— or

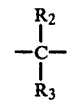

wherein $R_2$ or $R_3$ may be the same or different and are selected from the group consisting of hydrogen and $C_{1-4}$ alkyl; $R_4$ is —$OR_5$, wherein $R_5$ is selected from the group consisting of hydrogen, $C_{1-8}$ alkyl, cyclohexyl, benzyl and phenethyl, or

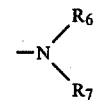

wherein $R_6$ and $R_7$ may be the same or different and are selected from the group consisting of hydrogen, $C_{1-4}$ alkyl, benzyl, phenethyl and together with the nitrogen atom, a heterocyclic group selected from the group consisting of a piperidino, morpholino, piperazino or thiazolino group; and m and n each are zero or a positive integer with m+n being no more than 11. The 2-oxyindole derivatives have excellent effects on the inhibition of platelet aggregation.

5 Claims, No Drawings

PLATELET AGGREGATION INHIBITING 2-OXYINDOLES, THEIR COMPOSITIONS AND METHOD OF USE

This is a division of application Ser. No. 588,475, filed June 19, 1975, now U.S. Pat. No. 4,070,470.

The present invention relates to novel benzcycloamide derivatives and to a pharmaceutical composition for treating thrombosis and embolism comprising the benzcycloamide derivatives as an active ingredient.

Hitherto, developments in medicine and pharmacy have contributed to the establishment of advanced therapeutic systems, whereby a number of serious diseases have been overcome. However, no effective and reliable therapeutic agent or method has yet been established for circulatory diseases, particularly, ischemic diseases, arterioscherosis and cerebral thrombosis. Since these circulatory diseases are often fatal, development of promising agents for preventing and treating these serious diseases has been of great concern to many people. The cause of these diseases is considered to be thrombosis as described in Hovig, T.: "Platelet Adhesion and Aggregation in Thrombosis": *Countermeasures* (Mammen, E. F., Anderson, G. F. & Barnhar, M. I. Eds.), p. 137 (1970); Bizzozero, J.: *Virchows Arch.*, 90, 261 (1882); and Eberth, J. C. & Schimmelbusch, C.: *Virchows Arch.*, 103, 39 (1886).

Thrombus is a clot formed by a coagulation of blood flowing in a blood vessel and the origin of the formation of thrombus and the symptoms caused by the thrombus are called thrombosis. A thrombus is useful in that damaged parts of a blood vessel are reinforced and in that continuous bleeding due to the activity of blood platelets as a "trigger" is prevented. On the other hand, the thrombus has negative aspects in that the thrombus obstructs the blood vessel cavity or obstructs the blood vessels of organs, limbs and the like when it is transported to other organs by blood flow thereby causing an embolus infarction. Therefore, thrombi formed in the main organs such as the heart, lungs, brain and the like are accompanied by fatal effects such as cerebral infarction (embolus), myocardiac infarction and pulmonary infarction. Further, in other diseases such as diabetes, malignant tumors, essential hypertension, valvular cardiac disease, Basedow's disease, aorta syndrome mucous tumor and the like, thrombi tend to be formed secondarily and also easily develop due to changes in the nature of blood per se, for example, coagulation acceleration state, etc. and blood vessel wall (Sozo Matsuoka, *Factors for Bleeding and Thrombosis*, page 206, published by Kinbara Publishing Co., 1969 and Kaname Kotake, "Thrombus Formation and Platelets", *Metabolism and Disease*, Vol. 10, No. 2, page 118, 1973).

Factors for thrombus formation include (1) change in the nature of the blood, (2) change in the blood flow and (3) change in blood vessel wall. Reference can be made to Tadashi Maekawa, *Ketsueki To Myakkan* (*Blood and Vessel*), Vol. 1, No. 4, pp 11–24, 1970. The normal flowing blood maintains an adequate dynamic balance between aggregation and dissociation of platelets as well as between coagulation and thrombolysis of the blood. Thrombosis can occur when this balance is lost due to stress or abnormal physiological conditions.

In recent years, the modern diet has very likely tended to induce arterioschlerosal disorders with a result in a possible increase in the occurrence of thrombosis. Under these circumstances, the development of chemotherapeutics for treating and preventing thrombosis has been greatly desired. For thrombosis, it is more effective to prevent the formation of thrombi by inhibiting further development of thrombi. Disorders induced by the secondarily formed thrombi can also be improved by administering therapeutic agents for alleviating the thrombi in combination with therapy for the fundamental disease.

As a result of various studies on the development of agents which are effective for preventing and treating thrombosis, it was found that 5-(2'-hydroxy-3-tert-butylamino)-propoxy-3,4-dihydrocarbostyril having the formula

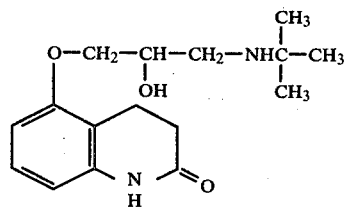

at low concentrations could specifically inhibit the aggregation of blood platelets and that this compound was very effective for preventing and treating thrombosis when administered orally or intravenously to mammals including humans. [Japanese Patent KOKAI (Laid-Open) No. 125,930/73]

An object of the present invention is to provide novel benzcycloamide derivatives which are useful as preventives for thrombosis and embolism.

Another object of the invention is to provide a pharmaceutical composition comprising the novel benzcycloamide derivatives as an active ingredient.

Further objects and advantages of the invention will become apparent from the following description.

According to the present invention, there is provided a novel benzcycloamide derivative represented by the general formula,

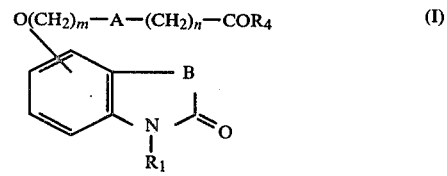

wherein $R_1$ is hydrogen, $C_{1-4}$ alkyl, $C_{2-4}$ alkenyl or aralkyl; B is —$CH_2$—, —$CH_2$—$CH_2$— or —CH=CH—; A is

(wherein $R_2$ and $R_3$ may be the same or different and are respectively hydrogen or $C_{1-4}$ alkyl) or —CH=CH—; $R_4$ is —$OR_5$ (wherein $R_5$ is hydrogen, $C_{1-8}$ alkyl, cycloalkyl or aralkyl) or

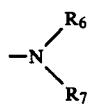

(wherein $R_6$ and $R_7$ may be the same or different and are respectively hydrogen, $C_{1-4}$ alkyl or aralkyl or may form together with the nitrogen atom a 5- or 6-membered heterocyclic group which may further contain a nitrogen, oxygen or sulfur atom); and m and n each are zero or a positive integer and m+n is no more than 11.

The novel benzcycloamide derivatives represented by the above-mentioned general formula (I) have excellent platelet aggregation-inhibiting activities and are useful as preventives for thrombosis and embolism. It has also been found that the benzcycloamide derivatives of the aforesaid general formula (I) have antiphlogistic effects.

In the general formula (I), $R_1$ is a hydrogen atom, a lower alkyl group such as a methyl, ethyl, propyl or butyl group, a lower alkenyl group such as allyl or crotyl group, or an aralkyl group such as a benzyl or phenethyl group. In A in the formula (I), $R_2$ and $R_3$ each are a hydrogen atom, or a lower alkyl group such as a methyl, ethyl, propyl or butyl group. Also, in $R_4$ in the formula (I), $R_5$ is a hydrogen atom or a straight chain or branched alkyl group such as a methyl, ethyl, propyl, butyl, amyl, hexyl or octyl group, or an aralkyl group such as a benzyl or phenethyl group, and $R_6$ and $R_7$, which may be the same or different, represent individually a lower alkyl group such as a methyl, ethyl, propyl or butyl group, or an aralkyl group such as a benzyl or phenethyl group, or may form together with the nitrogen atom a 5- or 6-membered heterocyclic group, which may further contain a nitrogen, oxygen or sulfur atom, for example, a piperidino, morpholino, piperazino or thiazolino group or the like.

When A is

in the benzcycloamide derivatives of the present invention, the carbon atom to which $R_2$ and $R_3$ are bonded may be asymmetric carbon atom and thereby there may be present optical isomers (dl-, d- and l-) of the derivatives. Also, when A is —CH=CH—, there are geometrical isomers (cis- and trans-) of the derivatives.

The benzcycloamide derivatives represented by the general formula (I) may be prepared by processes according to the reaction scheme shown below.

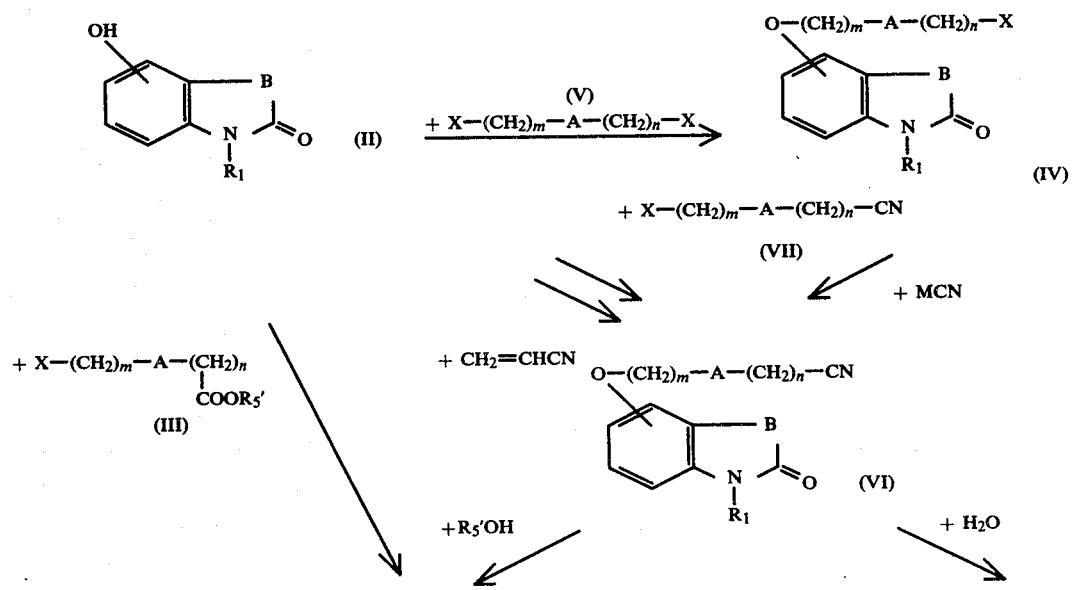

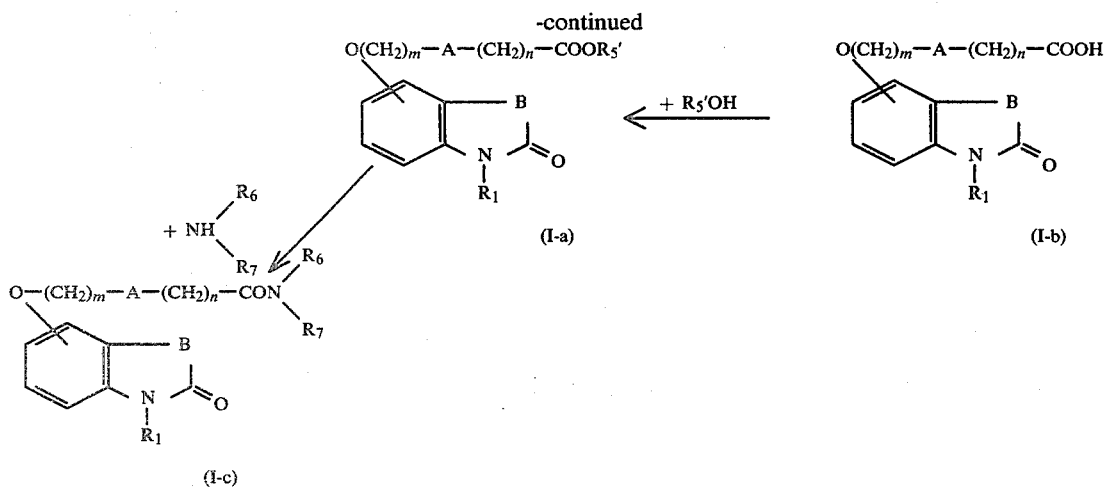

(I-c)

In the above-mentioned formulas, A, B, $R_1$, $R_6$, $R_7$, m and n are as defined above, and $R_5'$ is $C_{1-8}$ alkyl, cycloalkyl or aralkyl, X is halogen and M is an alkali metal.

In the first place, the compound represented by the general formula (I-b) can be prepared by hydrolyzing a benzcycloamide derivative represented by the general formula (VI). The above-mentioned hydrolysis reaction is carried out by a known process in the presence of a catalyst. As the catalyst, a conventional catalyst employed in usual hydrolysis reaction may be used. Concrete examples of such catalyst include basic compounds such as sodium hydroxide, potassium hydroxide and barium hydroxide; mineral acids such as sulfuric, nitric, hydrochloric and phosphoric acids; aromatic sulfonic acids such as naphthalenesulfonic and p-toluenesulfonic acids; and alkylsulfonic acids such as ethanesulfonic acid. In general, the hydrolysis reaction is effected in a solvent. As the solvent, there may be used any conventional solvent employed in usual hydrolysis reaction. Concrete examples of such solvent include water; alcohols such as methanol, ethanol, propanol, butanol and ethylene glycol; ketones such as acetone and methyl ethyl ketone; ethers such as dioxane and diethylene glycol monomethyl ether (monoglyme); and fatty acids such as acetic and propionic acids. The reaction temperature of said reaction is ordinarily from room temperature to 200° C., preferably from 50° to 150° C., and the reaction time is from 3 to 48 hours, preferably from 3 to 30 hours.

If necessary, the compounds represented by the general formula (I-b) may be converted into a compound of the general formula (I-a) by esterification reaction with an alcohol represented by the general formula $R_5'OH$. $R_5'$ in the alcohol represented by the general formula $R_5'OH$, which is the other starting material employed in the above-mentioned esterification reaction, is a straight chain or branched alkyl group such as a methyl, ethyl, propyl, butyl, amyl, hexyl or octyl group, or an aralkyl group such as a benzyl or phenethyl group. The reaction of the compound of the general formula (I-b) with the alcohol of the general formula $R_5'OH$ is carried out under conventional esterification reactions. This reaction is effected in the presence of a catalyst. As the catalyst, there may be used any conventional catalyst employed in usual esterification reaction. Concrete examples of such catalyst are hydrochloric acid gas; inorganic acids such as concentrated sulfuric acid, phosphoric acid, polyphosphoric acid, boron trifluoride and perchloric acid; organic acids such as trifluoroacetic acid, trifluoromethanesulfonic acid, naphthalenesulfonic acids, p-toluenesulfonic acid, benzenesulfonic acid and ethanesulfonic acid; anhydrides such as trifluoromethanesulfonic anhydride and trichloromethanesulfonic anhydride; thionyl chloride; acetone dimethyl acetal; and acidic ion exchange resins. The said reaction may be conducted either in the presence or absence of a solvent. The solvent may be any conventional solvent employed in usual esterification reaction. Concrete examples of such solvent include aromatic hydrocarbons such as benzene, toluene and xylene; halogenated hydrocarbons such as dichloromethane, dichloroethane, chloroform and carbon tetrachloride; and ethers such as diethyl ether, tetrahydrofuran, dioxane and ethylene glycol monomethyl ether. Further, the reaction is advantageously carried out by use of a drying agent such as anhydrous calcium chloride, anhydrous copper sulfate, anhydrous calcium sulfate or phosphorus pentoxide. The proportions of the compound represented by the general formula (I-b) and the alcohol represented by the general formula $R_5'OH$ may be properly selected. However, in case the reaction is effected in the absence of solvent, the alcohol is used in larger excess than in case the reaction is effected in the presence of a solvent, where the alcohol is used in an amount of 1 to 5 times, preferably 1 to 2 times, the moles of the compound of the general formula (I-b). The reaction temperature of said reaction is not particularly limited, but is ordinarily from −20° to 200° C., preferably from 0° to 150° C.

If necessary, the end compound of the present invention, which is represented by the general formula (I-a) may be converted into a compound represented by the general formula (I-c). Thus, the compound represented by the general formula (I'-a) is reacted with an amine of the general formula

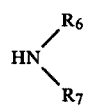

to give a compound represented by the general formula (I-c). This reaction may be effected in the presence of a suitable solvent. Examples of such solvent are water, methanol and ethanol. The reaction temperature and reaction time conditions are not particularly limited, and may be appropriately selected as occasion demands. Generally, however, the reaction is carried out at room temperature to 100° C., preferably at room temperature, for several hours. In this reaction, the amine is used in an equimolar amount or in excess. Generally, however, the amine is used in an amount of 5 to 10 times the moles of the fatty acid ester derivative.

Alternatively, the benzcycloamide derivative represented by the general formula (I-a) may be prepared by alcoholyzing a benzcycloamide derivative represented by the general formula (VI) with an alcohol of the general formula $R_5'OH$, and then adding water and subjecting the mixture to acid hydrolysis at a low temperature as low as 30° to 40° C. for 10 minutes. The reaction of the benzcycloamide derivative represented by the above-mentioned general formula (VI) with the alcohol represented by the general formula $R_5'OH$ is carried out under conventional alcoholysis reaction conditions. As the catalyst, there may be used any conventional catalyst employed in usual alcoholysis reaction. Concrete examples of such catalyst include hydrogen chloride; mineral acids such as concentrated sulfuric acid, phosphoric acid and nitric acid; and organic acids such as benzenesulfonic acid, p-toluenesulfonic acid and ethanesulfonic acid. The said reaction is conducted either in the presence or absence of a solvent. As the solvent, there may be used any conventional solvent employed in usual alcoholysis reaction. Concrete examples of such solvent include ethers such as diethyl ether, tetrahydrofuran, dioxane, monoglyme and diethylene glycol dimethyl ether (diglyme); aromatic hydrocarbons such as benzene, toluene and xylene; and aliphatic hydrocarbons such as n-pentane and n-hexane. The proportions of the compound represented by the general formula (VI) and the alcohol represented by the general formula $R_5'OH$ may suitably be selected from wide ranges. Generally, however, it is desirable that the latter is used in an amount of 1 to 5 times, preferably 1 to 2 times, the moles of the former. This reaction is effected at a temperature of −50° to 100° C., preferably −20° to 50° C., for a period of 1 to 48 hours, preferably 1 to 24 hours.

Further, the benzcycloamide derivative represented by the general formula (I-a) may be prepared by reacting a halogenated fatty acid ester of the general formula (III) with a hydroxybenzcycloamide derivative of the general formula (II). The fatty acid ester derivative of the general formula (III), which is used as a starting material, is a known compound. The reaction of the hydroxybenzcycloamide derivative represented by the general formula (II) with the halogenated fatty acid ester derivative represented by the general formula (III) is effected under conventional dehydrohalogenation reaction conditions. As the dehydrohalogenating agent, there may be used various basic compounds. Concrete examples thereof include inorganic bases such as sodium hydroxide, potassium hydroxide, sodium carbonate, potassium carbonate, sodium hydrogencarbonate, potassium hydrogencarbonate and silver carbonate; alkali metals such as sodium and potassium; alcoholates such as sodium methylate and sodium ethylate; and organic bases such as triethylamine, pyridine and N,N-dimethylaniline. The reaction may be effected either in the presence or absence of a solvent. As the solvent, any solvent may be used so far as it does not take part in the reaction. Concrete examples of such solvent are alcohols such as methanol, ethanol, propanol, butanol, and ethylene glycol; ethers such as dimethyl ether, tetrahydrofuran, dioxane, monoglyme and diglyme; ketones such as acetone and methyl ethyl ketone; aromatic hydrocarbons such as benzene, toluene and xylene; esters such as methyl acetate and ethyl acetate; and dipolar aprotic solvents such as N,N-dimethyl formamide (DMF), dimethyl sulfoxide (DMSO) and hexamethyl phosphoramide (HMPA). Further, the reaction is advantageously effected in the presence of a metal iodide such as sodium iodide or potassium iodide. The proportions of the compounds represented by the general formulas (II) and (III) may be properly decided. Ordinarily, however, it is desirable that the latter is used in an amount of 1 to 5 times, preferably 1 to 2 times, the moles of the former. The reaction temperature is not particularly limited, but is usually from room temperature to 200° C., preferably from 50° to 150° C., and the reaction time is generally from 1 to 30 hours, preferably from 1 to 15 hours.

The benzcycloamide derivative represented by the general formula (VI) may be obtained by reacting a hydroxybenzcycloamide derivative of the general formula (II) with a compound of the general formula (V) to form a compound represented by the general formula (IV), and then reacting the thus formed compound with a metal cyanide represented by the general formula MCN. The hydroxybenzcycloamide derivative represented by the general formula (II) is a known compound. The alkyldihalide represented by the general formula (V), which is the other starting material, is a known compound. The above-mentioned reaction of the hydroxybenzcycloamide represented by the general formula (II) with the compound represented by the general formula (V) is effected under conventional dehydrohalogenation reaction conditions. As the dehydrohalogenating agent, there may be used various basic compounds. Concrete examples thereof include inorganic bases such as sodium hydroxide, potassium hydroxide, sodium carbonate, potassium carbonate, sodium hydrogencarbonate, potassium hydrogencarbonate and silver carbonate; alkali metals such as sodium and potassium; alcoholates such as sodium methylate and sodium ethylate; and organic bases such as triethylamine, pyridine and N,N-dimethylaniline. The reaction may be carried out either in the presence or absence of a solvent. As the solvent, any solvent may be used so far as it does not take part in the reaction. Concrete examples of the solvent are alcohols such as methanol, ethanol, propanol, butanol and ethylene glycol; ethers such as diethyl ether, tetrahydrofuran, dioxane, monoglyme and diglyme; ketones such as acetone and methyl ethyl ketone; aromatic hydrocarbons such as benzene, toluene and xylene; esters such as methyl acetate and ethyl acetate; dipolar aprotic solvents such as DMF, DMSO and HMPA; and water. Further, the reaction is advantageously carried out in the presence of a metal iodide such as sodium iodide or potassium iodide. The proportions of the compounds represented by the general formulas (II) and (V) may be properly decided. Ordinarily, however, it is desirable that the latter is used in an amount of 1 to 5 times, preferably 1 to 2 times, the moles of the former. The reaction temperature is not particularly limited, but is usually from room temperature to 200° C., preferably from 50° to 150° C., and the reaction time is generally from 1 to 30 hours, preferably from 1 to 15 hours.

In the next place, the compound represented by the general formula (IV) is reacted, either in the presence or absence of a solvent, with a metal cyanide represented by the general formula MCN such as, for example, sodium cyanide, potassium cyanide, silver cyanide or cuprous cyanide. In general, it is desirable that the reaction is carried out in the presence of a solvent. As the solvent, and solvent may be used so far as it does not take part in the reaction. Concrete examples of such solvent include water; alcohols such as methanol, ethanol, propanol and ethylene glycol; ketones such as acetone and methyl ethyl ketone; ethers such as dioxane, tetrahydrofuran, monoglyme and diglyme; aromatic hydrocarbons such as benzene, toluene and xylene; dipolar aprotic solvents such as DMF, DMSO and HMPA; liquid hydrogen cyanide; and liquid ammonia. This reaction is advantageously effected in the presence of a metal iodide such as potassium iodide or sodium iodide. The proportions of the compounds represented by the general formulas (IV) and MCN may be properly selected. Ordinarily, however, it is desirable that the latter is used in an amount of 1 to 5 times, preferably 1 to 2 times, the moles of the former. The reaction temperature is not particularly limited, but is usually from room temperature to 250° C., preferably from 50° to 150° C., and the reaction time is from 30 minutes to 30 hours, preferably from 30 minutes to 15 hours.

Further, the benzcycloamide derivative represented by the general formula (VI) may be prepared also by reacting a hydroxybenzcycloamide derivative of the general formula (II) with a compound of the general formula (VII). The compound of the general formula (VII), which is the other starting compound, is a known compound. The reaction of the hydroxybenzcycloamide represented by the general formula (II) with the compound represented by the general formula (VII) is carried out under conventional dehydrohalogenation reaction conditions. As the dehydrohalogenating agent, there may be used various basic compounds. Concrete examples thereof are inorganic bases such as sodium hydroxide, potassium hydroxide, sodium carbonate, potassium carbonate, sodium hydrogencarbonate, potassium hydrogencarbonate and silver carbonate; alkali metals such as sodium and potassium; alcoholates such as sodium methylate and sodium ethylate; and organic bases such as triethylamine, pyridine and N,N-dimethylaniline. This reaction may be conducted either in the presence or absence of a solvent. As the solvent, any solvent may be used so far as it does not take part in the reaction. Concrete examples of such solvent include alcohols such as methanol, ethanol, propanol, butanol and ethylene glycol; ethers such as diethyl ether, tetrahydrofuran, dioxane, monoglyme and diglyme; ketones such as acetone and methyl ethyl ketone; aromatic hydrocarbons such as benzene, toluene and xylene; esters such as methyl acetate and ethyl acetate; and dipolar aprotic solvents such as DMF, DMSO and HMPA. The reaction is advantageously carried out in the presence of a metal iodide such as sodium iodide or potassium iodide. The proportions of the compounds represented by the general formulas (II) and (VII) may be properly decided. Ordinarily, however, it is desirable that the latter is used in an amount of 1 to 5 times, preferably 1 to 2 times, the moles of the former. The reaction temperature is not particularly limited, but is usually from room temperature to 200° C., preferably from 50° to 150° C., and the reaction time is generally from 1 to 30 hours, preferably from 1 to 15 hours.

Further, the compound represented by the general formula (VI) may alternatively be prepared by reacting a hydroxybenzcycloamide derivative represented by the general formula (II) with acrylonitrile. This reaction is usually carried out in a solvent in the presence of a catalyst. Examples of the catalyst are sodium methylate, sodium ethylate, Triton B, sodium hydroxide, potassium hydroxide and potassium carbonate. Examples of the solvent are benzene, dioxane, pyridine and acrylonitrile. Among these solvents, acrylonitrile is most preferable. In the above-mentioned reaction, the acrylonitrile is used in an amount of 1 to several times the moles of the hydroxybenzcycloamide derivative. The reaction proceeds even at room temperature to 150° C., but is preferably carried out at 50° to 100° C., in general.

The benzcycloamide derivative represented by the general formula (I-a) which was obtained by the present invention may be converted, if necessary, by hydrolysis into a corresponding free carboxylic acid represented by the general formula (I-b). The above-mentioned hydrolysis reaction is ordinarily carried out according to a known process in the presence of a catalyst. As the catalyst, there is used a conventional catalyst employed in usual hydrolysis reaction. Concrete examples of such catalyst include basic compounds such as sodium hydroxide, potassium hydroxide and barium hydroxide; mineral acids such as sulfuric, hydrochloric and nitric acids; and organic acids such as acetic acid and aromatic sulfonic acids. Generally, the said reaction is effected in a solvent. As the solvent, there may be used any conventional solvent employed in usual hydrolysis reaction. Concrete examples of such solvent include water, methanol, ethanol, isopropanol, acetone, methyl ethyl ketone, dioxane, ethylene glycol and acetic acid. The reaction temperature of the said reaction is not particularly limited, but is desirably from room temperature to 200° C.

The benzcycloamide derivative of the general formula,

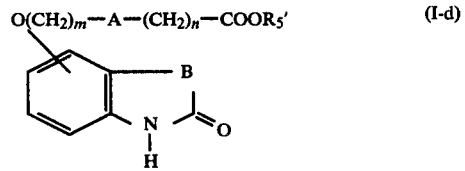

(I-d)

wherein A, B, $R_5'$, m and n are as defined above, obtained according to the present invention may be converted, if necessary, into the benzcycloamide derivative of the general formula,

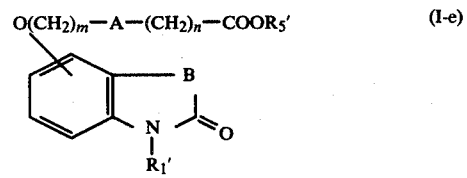

(I-e)

wherein A, B, $R_5'$, m and n are as defined above and $R_1'$ is $C_{1-4}$ alkyl, $C_{2-4}$ alkenyl or aralkyl, by reacting the benzcycloamide derivative of the general formula (I-d) with a halogenide compound represented by the general formula $R_1'X$ wherein $R_1'$ and X are as defined above. Thus, the benzcycloamide derivative represented by the general formula (I-d) is formed into an alkali metal salt at its 1-position nitrogen, and then condensed with the halogenide compound of the general formula $R_1'X$, whereby the benzcycloamide derivative of the general formula (I-e) can be obtained. In carrying out the above-mentioned reaction, the alkali metal salt of the compound (I-d) is prepared by condensing the compound (I-d) at 0° to 200° C., preferably at room temperature to 50° C., with an alkali metal compound such as sodium hydride, potassium hydride, sodium azide, metallic sodium or metallic potassium, in a suitable solvent, e.g. a benzene type solvent (benzene, toluene or xylene), n-hexane, cyclohexane, an ether type solvent (diethyl ether, 1,2-dimethoxyethane or dioxane) or a dipolar aprotic solvent (DMF, HMPA or DMSO), preferably in DMF, DMSO or HMPA. The condensate reaction of the thus prepared alkali metal salt of the compound (I-d) with the compound of the formula $R_1'X$ proceeds successfully when the two are reacted at room temperature in, for example, a DMF solvent. In this case, the amount of the alkali metal compound is 1 to 5 times, preferably 1 to 3 times, the moles of the compound of the formula (I-d), while the amount of the halogenide compound is 1 to 5 times, preferably 1 to 2 times, the moles of the compound of the formula (I-d).

Also, the benzcycloamide derivative of the general formula,

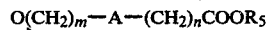
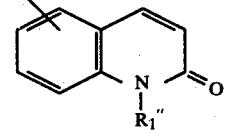

(I-f)

wherein A, $R_5$, m and n are as defined above and $R_1''$ is a hydrogen atom, a lower alkyl group such as methyl, ethyl, propyl or butyl group, or an aralkyl group such as a benzyl or phenethyl group, obtained according to the present invention may be converted, if necessary, by reduction into a corresponding 3,4-dihydrobenzcycloamide derivative represented by the general formula,

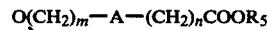
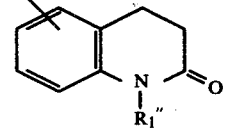

(I-g)

wherein A, $R_1''$, $R_5$, m and n are as defined above. The reaction of the compound represented by the general formula (I-f) is ordinarily carried out by hydrogenating said compound in a suitable solvent in the presence of a conventional catalyst. The catalyst used in this case is, for example, a platinum catalyst such as platinum wire, platinum rod, platinum sponge, platinum black, platinum oxide or colloidal platinum; a palladium catalyst such as palladium sponge, palladium black, palladium oxide, palladium barium sulfate, palladium barium carbonate, palladium carbon, palladium silica gel or colloidal palladium; a platinum group metal catalyst such as asbestos-attached rhodium, iridium, colloidal rhodium, ruthenium or colloidal iridium; a nickel catalyst such as reduced nickel, nickel oxide, Raney nickel, Urushibara nickel, nickel catalyst formed by thermal decomposition of nickel formate, or nickel boride; a cobalt catalyst such as reduced cobalt, Raney cobalt or Urushibara cobalt; an iron catalyst such as reduced iron or Raney iron; a copper catalyst such as reduced copper, Raney copper or Ullman copper; or other metal catalyst such as zinc. Further, the solvent used in the reaction is, for example, a lower alcohol such as methanol, ethanol or isopropanol; water; acetic acid; an acetic acid ester such as methyl acetate or ethyl acetate; ethylene glycol; an ether such as diethyl ether, tetrahydrofuran or dioxane; an aromatic hydrocarbon such as toluene, benzene or xylene; a cycloalkane such as cyclopentane or cyclohexane; or a n-alkane such as n-hexane or n-pentane. The reaction successfully progresses at atmospheric hydrogen pressure or under pressure, preferably 1 to 20 atm., and at room temperature to below the boiling point of the solvent used, preferably at room temperature to 100° C.

Further, the 3,4-dihydrobenzcycloamide derivative of the general formula,

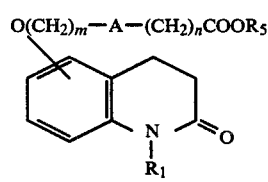

(I-h)

wherein A, $R_1$, $R_5$, m and n are as defined above, obtained according to the present invention may be converted, if necessary, by dehydrogenation into a benzcycloamide derivative represented by the general formula,

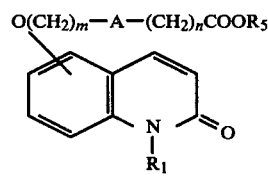

(I-i)

wherein A, $R_1$, $R_5$, m and n are as defined above. The dehydrogenation of the compound (I-h) is carried out by use of an oxidizing agent in the presence of a suitable solvent. The oxidizing agent used in the above is a benzoquinone such as DDQ (2,3-dichloro-5,6-dicyanobenzoquinone) or chloranil (2,3,5,6-tetrachlorobenzoquinone); a hydrogenation catalyst such as selenium dioxide, palladium carbon, palladium black, platinum oxide or Raney nickel; or a brominating agent such as NBS (N-bromosuccimide) or bromine. Further, the solvent used in the above is an ether such as dioxane, tetrahydrofuran, methoxy ethanol or dimethoxy ethane; an aromatic hydrocarbon such as benzene, toluene, xylene or cumene; a halogenated hydrocarbon such as dichloromethane, dichloroethane, chloroform or carbon tetrachloride; an alcohol such as butanol, amyl alcohol or hexanol; or a dipolar aprotic solvent such as DMF, DMSO or HMPA. The reaction temperature is in the range from room temperature to 300° C., preferably from 50° to 200° C., and the reaction time is in the range from 1 to 48 hours, preferably from 1 to 20 hours. The proportion of the oxidizing agent used is 1 to 5 times, preferably 1 to 2 times, the moles of the compound (I-i) in the case of a benzoquinone or a brominating agent, and is a usual catalytic amount in the case of a hydrogenation catalyst.

All the benzcycloamide derivatives represented by the aforesaid general formulas (I) are novel compounds having excellent platelet aggregation-inhibiting effects and are useful as preventives for thrombosis. Platelet aggregation-inhibiting effects and toxicity (LD$_{50}$, mg/kg) of typical derivatives among the above-mentioned novel benzcycloamide derivatives obtained according to the present invention are as shown below. Compounds tested:

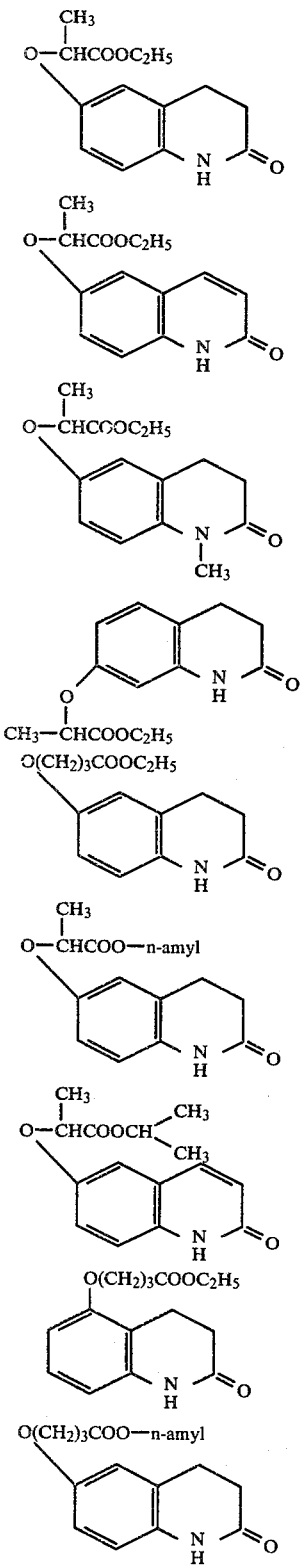

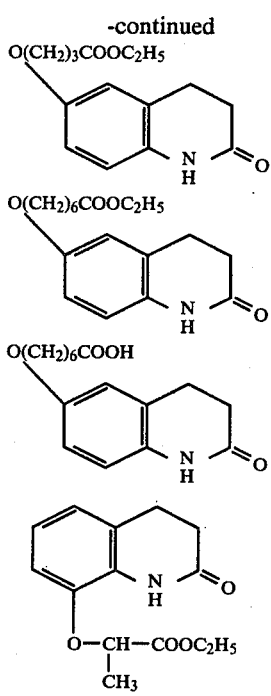

Table 1
Inhibition effect of benzcycloamide derivative on collagen-induced aggregation in rabbit platelet

| Compound | Concentration of test compound solution | | | | |
|---|---|---|---|---|---|
| | $10^{-8}$ M | $10^{-7}$ M | $10^{-6}$ M | $10^{-5}$ M | $10^{-4}$ M |
| A | 0% | — | 2% | 20% | 71% |
| B | 0 | — | −6 | 12 | 67 |
| C | 9 | — | 0 | — | 36 |
| D | 3 | — | 8 | — | 2 |
| E | — | — | 8 | 38 | 92 |
| F | — | — | 0 | 8 | 88 |
| G | — | — | 3 | 25 | 55 |
| H | — | — | 5 | 8 | 90 |
| I | — | — | 6 | 22 | 48 |
| J | — | — | 18 | 86 | 100 |
| K | — | — | 6 | 13 | 31 |
| L | — | — | 2 | 14 | 15 |
| M | 7 | — | 2 | — | 5 |

Table 2
Inhibition effect of benzcycloamide derivatives on ADP-induced aggregation in rabbit platelet

| Compound | Concentration of test compound solution | | | | |
|---|---|---|---|---|---|
| | $10^{-8}$ M | $10^{-7}$ M | $10^{-6}$ M | $10^{-5}$ M | $10^{-4}$ M |
| A | —% | —% | 5% | 25% | 57% |
| B | 14 | — | −6 | 54 | 86 |
| C | 9 | — | 0 | — | 36 |
| D | 14 | — | 14 | — | −18 |
| E | — | 8 | 10 | 97 | 100 |
| F | — | — | 20 | 79 | 100 |
| G | — | — | 7 | 38 | 74 |
| H | — | — | 2 | 18 | 65 |
| I | — | 8 | 0 | 58 | 82 |
| J | — | −4 | 25 | 90 | 100 |
| K | — | 7 | 10 | 15 | 37 |
| L | — | −10 | 7 | 8 | 13 |
| M | 11 | — | 11 | — | 3 |

Table 3

Toxicity of benzcycloamide derivatives in mouse

| Compound | LD$_{50}$ (mg/kg) Male mouse | LD$_{50}$ (mg/kg) Female mouse |
|---|---|---|
| E | >1000 | >1000 |
| K | 750–1000 | 500–1000 |

The aggregation inhibitory activity was determined using an AG-II type aggregometer (made by Bryston Manufacturing Co.). A blood sample was withdrawn from rabbits as a mixture of sodium citrate and whole blood in a proportion of 1:9 by volume and centrifuged at 1000 rpm for 10 minutes to obtain a platelet rich plasma (PRP). The resulting PRP was separated, and the remaining blood sample was further centrifuged at 3000 rpm for 15 minutes to obtain a platelet poor plasma (PPP).

The number of platelets in the PRP was counted in accordance with the Brecher-Clonkite Method, and the PRP was diluted with the PPP to prepare a PRP sample containing platelets in an amount of 300,000/mm$^2$ for an adenosine diphosphate (ADP)-induced aggregation test and a PRP sample containing platelets in an amount of 450,000/mm$^2$ for a collagen-induced aggregation test.

0.01 ml of a solution of a test compound having a predetermined concentration (as shown in the Tables below) was then added to 0.6 ml of the PRP sample obtained above and the mixture was incubated at a temperature of 37° C. for 1 minute. Then 0.07 ml of an ADP or collagen solution was added to the mixture. The mixture was then subjected to a transmittance determination and changes in the transmittance of the mixture were recorded using aggregometer at a stirrer rotation rate of 1100 rpm. In this test, Auren Beronal buffer (pH 7.35) was used for the preparation of solutions of ADP, collagen and the test compounds. ADP was adjusted to a concentration of $7.5 \times 10^{-5}$ M, and the collagen solution was prepared by triturating 100 mg of collagen with 5 ml of the above buffer and the supernatant obtained was used as a collagen inducer. Adenosine and acetylsalicylic acid were used as controls for the ADP-induced aggregation test and the collagen-induced aggregation test, respectively. The aggregation inhibitory activity was determined in terms of the percent inhibition (%) with respect to the aggregation ratio of controls. The aggregation ratio can be calculated by the following equation:

$$\text{Aggregation Ratio} = \frac{c - a}{b - a} \times 100$$

Wherein:
"a" is the optical density of the PRP,
"b" is the optical density of the PRP having incorporated therein a test compound and an aggregation inducer, and
"c" is the optical density of the PPP.

The benzcycloamide compounds of the present invention can be administered, either as they are or in administration unit forms in combination with conventional pharmaceutical carriers, to animals, mammals and humans. Suitable administration unit forms include such oral administration forms as tablets, capsules, powders, granules and oral solutions; sublingual and buccal administration forms; and parenteral administration forms useful for subcutaneous, intramulscular or intraveneous administration. In order to attain a desired effect, the dose of the active ingredient administered is variable over such a wide range as from about 0.1 mg. to about 100 mg. per kg. body weight per day. Each unit dose may contain about 1 mg. to 500 mg. of active ingredient in combination with a pharmaceutical carrier. Such suitable dose can be administered 1 to 4 times a day.

In the preparation of such solid composition as tablets, the main active ingredient is mixed with a pharmaceutical vehicle such as gelatin, starch, lactose, magnesium stearate, talc, gum arabic, or the like. Tablets may be coated with sucrose or other suitable materials or treated in other manner so as to display an extended or delayed activity and to continuously release a predetermined amount of drug. A capsule preparation is obtained by mixing the active ingredient with an inert pharmaceutical filler or diluent a filling the resulting mixture into rigid gelatin capsules or soft capsules. A syrup or elixir preparation may contain the active ingredient together with sucrose or the like sweetening, methyl- and propyl-parabens as antiseptics, and suitable colorant and seasoning.

A parenteral liquid is prepared by dissolving the active ingredient in a sterilized liquid vehicle. Preferable as the vehicle is water or brine. A composition having desired transparency, stability, and parenteral use adaptability is prepared by dissolving about 0.1 mg. to about 3 g. of the active ingredient in a non-volatile liquid-polyethylene glycol mixture having a molecular weight of 200 to 1,500 which is soluble both in water and in organic liquids. The resulting solution is advantageously incorporated with a lubricant such as, for example, sodium carboxymethyl cellulose, methyl cellulose, polyvinyl pyrrolidone or polyvinyl alcohol. Further, the solution may contain bactericides and fungicides such as, for example, parabens, benzyl alcohol, phenol or thimerosal. If desired, an isotonic agent such as sugar or sodium chloride, a local anesthetic, a stabilizer or a buffer agent may also be added thereto. In order to further enhance its stability, the parenteral composition may be freed from water by the freeze-drying technique that is thoroughly known to the art of this field. The powder formed by the freeze-drying may be reconstructed immediately before use.

Preparation of Tablets 1,000 Tablets for oral use, each containing 5 mg. of 6-(1-ethoxycarboxy)propoxy-3,4-dihydrocarbostyril, are prepared from the following components:

| | | |
|---|---|---|
| (a) | 6-(1-Ethoxycarboxy)propoxy-3,4-dihydrocarbostyril | 5 g. |
| (b) | Lactose, J.P. | 50 g. |
| (c) | Corn starch, J.P. | 25 g. |
| (d) | Crystalline cellulose, J.P. | 25 g. |
| (e) | Methyl cellulose, J.P. | 1.5 g. |
| (f) | Magnesium stearate, J.P. | 1 g. |

The above-mentioned 6-(1-ethoxycarboxy)propoxy-3,4-dihydrocarbostyril, lactose, corn starch and crystalline cellulose are sufficiently mixed together. The resulting mixture is granulated by adding a 5.0% aqueous solution of the methyl cellulose. The granules are passed through a 200 mesh sieve and then dried carefully. The dried granules are passed through a 200 mesh sieve, admixed with the magnesium stearate, and then compressed into tablets.

Preparation of Capsules 1,000 Pieces of two-piece rigid gelatin capsules for oral use, each containing 10 mg. of 6-(1-ethoxycarboxy)propoxy-3,4-dihydrocarbostyril, are prepared from the following components:

| (a) | 6-(1-Ethoxycarboxy)propoxy-3,4-dihydrocarbostyril | 10 g. |
|---|---|---|
| (b) | Lactose, J.P. | 80 g. |
| (c) | Starch, J.P. | 30 g. |
| (d) | Talc, J.P. | 5 g. |
| (e) | Magnesium stearate, J.P. | 1 g. |

The above-mentioned components are finely ground, and the resulting particles are sufficiently mixed together to form a homogeneous mixture. Subsequently, the mixture is filled into rigid gelatin capsules of optional size to prepare capsules for oral administration.

Preparation of Injections

A sterile aqueous solution suitable for parenteral use is prepared from the following components:

| (a) | 6-(1-Ethoxycarboxy)propoxy-3,4-dihydrocarbostyril | 1 g. |
|---|---|---|
| (b) | Polyethylene Glycol 4000, J.P. | 0.3 g. |
| (c) | Sodium chloride | 0.9 g. |
| (d) | Polyoxyethylene derivative of sorbitan monooleate, J.P. | 0.4 g. |
| (e) | Sodium metabisulfite | 0.1 g. |
| (f) | Methyl-paraben, J.P. | 0.18 g. |
| (g) | Propyl-paraben, J.P. | 0.02 |
| (h) | Distilled water for injections sufficient to make | 100 ml. |

A mixture comprising the above-mentioned parabens, sodium metabisulfite and sodium chloride is dissolved in about 0.5 time the volume thereof of distilled water for injections with stirring at 80° C. The resulting solution is cooled to below 40° C., and the above-mentioned active ingredient, and then the Polyethylene Glycol 4000 and the polyoxyethylene derivative of sorbitan monooleate are dissolved in the solution. Subsequently, the solution is adjusted to the final volume by addition of the distilled water for injections, and then sterilized by sterile filtration through an appropriate filter paper. 1 Milliliter of the thus prepared solution contains 10 mg. of 6-(1-ethoxycarboxy)propoxy-3,4-dihydrocarbostyril as active ingredient.

EXAMPLE 1

1.64 Grams of 5-(2'-cyanoethoxy)-3,4-dihydrocarbostyril was added to 50 ml. of concentrated hydrochloric acid, and the resulting mixture was refluxed for 5 hours. Thereafter, the reaction liquid was cooled to deposit crystals. The deposited crystals were recovered by filtration and then recrystallized from water to obtain 1.5 g. of 5-(2'-carboxyethoxy)-3,4-dihydrocarbostyril in the form of colorless needle-like crystals, m.p. 221°–224° C.

EXAMPLE 2

1 Gram of 6-(2'-cyanoethoxy)-3,4-dihydrocarbostyril was added to 30 ml. of concentrated hydrochloric acid, and the resulting mixture was refluxed for 4 hours. Thereafter, the reaction liquid was cooled to deposit crystals. The deposited crystals were recovered by filtration and then recrystallized from water to obtain 0.2 g. of 6-(2'-carboxyethoxy)-3,4-dihydrocarbostyril in the form of colorless needle-like crystals, m.p. 188°–190.5° C.

EXAMPLE 3

0.4 Gram of 7-(2'-cyanoethoxy)-3,4-dihydrocarbostyril was added to 25 ml. of concentrated hydrochloric acid, and the resulting mixture was refluxed for 4 hours. Thereafter, the reaction liquid was concentrated to dryness under reduced pressure, and the concentrate was recrystallized from water to obtain 0.2 g. of 7-(2'-carboxyethoxy)-3,4-dihydrocarbostyril in the form of colorless scale-like crystals, m.p. 161°–164.5° C.

EXAMPLE 4

1 Gram of 8-(2'-cyanoethoxy)-3,4-dihydrocarbostyril was added to 25 ml. of concentrated hydrochloric acid, and the resulting mixture was refluxed for 5 hours. Thereafter, the reaction liquid was cooled to deposit crystals. The deposited crystals were recovered by filtration and then recrystallized from water to obtain 0.7 g. of 8-(2'-carboxyethoxy)-3,4-dihydrocarbostyril in the form of colorless needle-like crystals, m.p. 247°–248.5° C.

EXAMPLE 5

18 Grams of N-ethyl-5-(3'-cyano)propoxy-3,4-dihydrocarbostyril was added to 250 ml. of a 2 N-aqueous sodium hydroxide solution, and the resulting mixture was refluxed with stirring for 17 hours. Thereafter, the reaction liquid was cooled and then acidified by addition of hydrochloric acid to deposit crystals. The deposited crystals were recovered by filtration, washed with water and then recrystallized from ethyl acetate to obtain 14 g. of N-ethyl-5-(3'-carboxy)propoxy-3,4-dihydrocarbostyril in the form of colorless needle-like crystals, m.p. 96°–98° C.

EXAMPLE 6

18 Grams of 6-(3'-cyano)propoxy-3,4-dihydrocarbostyril was added to 300 ml. of a 2 N-aqueous potassium hydroxide solution, and the resulting mixture was refluxed with stirring for 18 hours. Thereafter, the reaction liquid was cooled and then acidified by addition of hydrochloric acid to deposit crystals. The deposited crystals were recovered by filtration, washed with water and then recrystallized from methanol to obtain 17.5 g. of 6-(3'-carboxy)propoxy-3,4-dihydrocarbostyril in the form of colorless amorphous solids, m.p. 218°–220° C.

EXAMPLES 7–37

According to Example 6, such compounds as shown in Tables 4 and 5 were obtained.

Table 4

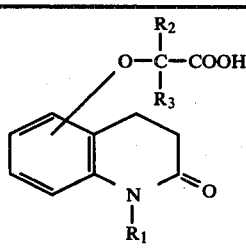

| Example No. | Position of substituent | $R_1$ | $R_2$ | $R_3$ | Properties Crystal form | m.p. °C. |
|---|---|---|---|---|---|---|
| 7 | 5 | H | H | H | Colorless needle-like crystals | 278–280 |
| 8 | 5 | H | $CH_3$ | H | Colorless needle-like crystals | 246–248.5 |
| 9 | 5 | $CH_3$ | H | H | Colorless needle-like crystals | 196–198.5 |
| 10 | 5 | H | $CH_3$ | $CH_3$ | Colorless needle-like crystals | 191–192.5 |
| 11 | 6 | H | H | H | Colorless needle-like crystals | 241.5–244 |
| 12 | 6 | H | $CH_3$ | H | Colorless needle-like crystals | 207–210.5 |
| 13 | 6 | H | $CH_3$ | $CH_3$ | Colorless needle-like crystals | 172-175.5 |
| 14 | 7 | H | H | H | Colorless needle-like crystals | 262–264 |
| 15 | 7 | H | $CH_3$ | $CH_3$ | Colorless needle-like crystals | 205–206.5 |
| 16 | 8 | H | H | H | Colorless needle-like crystals | 227.5–229 |
| 17 | 8 | H | $CH_3$ | H | Colorless needle-like crystals | 184–186 |
| 18 | 8 | H | $CH_3$ | $CH_3$ | Colorless needle-like crystals | 232.5–236.5 |
| 19 | 5 | H | $C_2H_5$ | H | Colorless needle-like crystals | 247–248 |
| 20 | 5 | $CH_3$ | $CH_3$ | H | Colorless needle-like crystals | 148–149 |
| 21 | 5 | $CH_2-CH=CH_2$ | $CH_3$ | H | Colorless needle-like crystals | 144–145 |
| 22 | 5 | $CH_2-C_6H_5$ | $CH_3$ | H | Colorless needle-like crystals | 157–160 |
| 23 | 6 | H | $C_2H_5$ | H | Colorless needle-like crystals | 197–198 |
| 24 | 6 | $CH_2-C_6H_5$ | $CH_3$ | H | Colorless needle-like crystals | 148–149 |
| 25 | 7 | H | $C_2H_5$ | H | Colorless needle-like crystals | 194–197 |
| 26 | 7 | $C_2H_5$ | $C_2H_5$ | H | Colorless needle-like crystals | 78–79 |
| 27 | 8 | $CH_2-C_6H_5$ | $C_2H_5$ | H | Colorless needle-like crystals | 148–150 |
| 28 | 8 | H | $C_2H_5$ | H | Colorless needle-like crystals | 175–180 |

Table 5

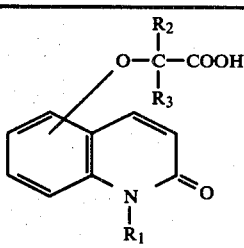

| Example No. | Position of substituent | $R_1$ | $R_2$ | $R_3$ | Properties Crystal form | m.p. °C. |
|---|---|---|---|---|---|---|
| 29 | 5 | H | $CH_3$ | H | Colorless flake- | 280–281 |

Table 5-continued

| Example No. | Position of substituent | $R_1$ | $R_2$ | $R_3$ | Crystal form | m.p. °C. |
|---|---|---|---|---|---|---|
| 30 | 5 | H | $C_2H_5$ | H | Colorless needle-like crystals | 282–284 |
| 31 | 5 | $CH_3$ | $CH_3$ | H | Colorless needle-like crystals | 225–227 |
| 32 | 6 | H | $CH_3$ | H | Colorless needle-like crystals | 276–279 |
| 33 | 6 | $CH_2-C_6H_5$ | $CH_3$ | H | Colorless needle-like crystals | 186–187 |
| 34 | 7 | H | $CH_3$ | $CH_3$ | Colorlesse needle-like crystals | 216–218 |
| 35 | 7 | $C_2H_5$ | $C_2H_5$ | H | Colorless needle-like crystals | 137–139 |
| 36 | 8 | H | H | H | Colorless needle-like crystals | 278–281 |
| 37 | 8 | H | $CH_3$ | $CH_3$ | Colorless needle-like crystals | 217–218 |

EXAMPLE 38

To 15 g. of 5-(6'-cyano)hexyloxy-3,4-dihydrocarbostyril were added 150 ml. of water, 150 ml. of dioxane and 25 g. of sodium hydroxide, and the resulting mixture was refluxed with stirring for 20 hours. Thereafter, the reaction liquid was cooled and then acidified by addition of hydrochloric acid to deposit crystals. The deposited crystals were recovered by filtration, washed with water and then recrystallized from methanol to obtain 13 g. of 5-(6'-carboxy)hexyloxy-3,4-dihydrocarbostyril in the form of colorless needle-like crystals, m.p. 138°–142° C.

EXAMPLES 39–60

According to Example 5, such compounds as shown in Tables 6 and 7 were obtained.

Table 6

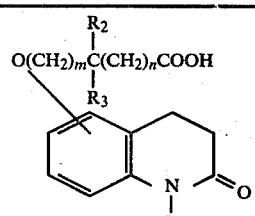

| Example No. | Position of substituent | $R_1$ | $(CH_2)_m\overset{R_2}{\underset{R_3}{C}}(CH_2)_n$ | Crystal form | m.p. (°C.) |
|---|---|---|---|---|---|
| 39 | 5 | H | $(CH_2)_3$ | Colorless amorphous solid | 212–215 |
| 40 | 5 | H | $(CH_2)_4$ | Colorless amorphous solid | 175–177 |
| 41 | 5 | H | $(CH_2)_{10}$ | Colorless needle-like crystals | 132–133 |
| 42 | 5 | H | $CH_2CH(CH_3)CH_2$ | Colorless needle-like crystals | 195–198 |
| 43 | 5 | $CH_2C_6H_5$ | $(CH_2)_2$ | Colorless amorphous solid | 185–188 |
| 44 | 5 | $CH_2CH=CH_2$ | $(CH_2)_3$ | Colorless needle-like crystals | 108–110 |
| 45 | 6 | H | $(CH_2)_4$ | Colorless needle-like crystals | 185–187 |
| 46 | 6 | H | $(CH_2)_6$ | Colorless amorphous solid | 179–181 |
| 47 | 6 | H | $(CH_2)_{10}$ | Colorless needle-like crystals | 140–143 |

Table 6-continued $$\text{O(CH}_2)_m\overset{R_2}{\underset{R_3}{C}}(\text{CH}_2)_n\text{COOH}$$

(structure: 3,4-dihydrocarbostyril with O(CH2)mC(R2)(R3)(CH2)nCOOH substituent on benzene ring, N-R1)

| Example No. | Position of substituent | R₁ | R₂ / R₃ $(CH_2)_m\overset{R_2}{\underset{R_3}{C}}(CH_2)_n$ |  | Properties |  |
|---|---|---|---|---|---|---|
|  |  |  | R₂ | R₃ | Crystal form | m.p. (°C.) |
| 48 | 6 | H | CH₃ | CH₂CHCH₂ | Colorless amorphous solid | 173–174 |
| 49 | 6 | H | CH₃ | CH₂CH₂CH | Colorless needle-like crystals | 201–203 |
| 50 | 6 | CH₃ |  | (CH₂)₃ | Colorless needle-like crystals | 156–159 |
| 51 | 6 | CH₂—CH=CH₂ |  | (CH₂)₆ | Colorless needle-like crystals | 95–97 |
| 52 | 7 | H |  | (CH₂)₃ | Colorless needle-like crystals | 207–209 |
| 53 | 7 | H |  | (CH₂)₅ | Colorless needle-like crystals | 181–183 |
| 54 | 8 | H |  | (CH₂)₆ | Colorless needle-like crystals | 192–195 |

Table 7

$$\text{O(CH}_2)_m\text{CH}(R_2)(\text{CH}_2)_n\text{COOH}$$

(structure: carbostyril with O(CH2)mCH(R2)(CH2)nCOOH substituent on benzene ring, N-R1)

| Example No. | Position of substituent | R₁ | R₂ $(CH_2)_mCH(CH_2)_n$ | Properties |  |
|---|---|---|---|---|---|
|  |  |  |  | Crystal form | m.p.(°C.) |
| 55 | 5 | H | (CH₂)₃ | Colorless needle-like crystals | 241–243 |
| 56 | 5 | H | (CH₂)₄ | Colorless needle-like crystals | 196–197 |
| 57 | 5 | H | (CH₂)₆ | Colorless needle-like crystals | 163–165 |
| 58 | 5 | C₂H₅ | (CH₂)₃ | Colorless needle-like crystals | 125–126 |
| 59 | 6 | H | (CH₂)₃ | Colorless needle-like crystals | 257–258 |
| 60 | 6 | H | (CH₂)₆ | Colorless needles-like crystals | 201–203 |

EXAMPLE 61

2.5 Grams of 5-(1'-carboxy)propoxy-3,4-dihydrocarbostyril was added to 50 ml. of ethanol saturated with hydrogen chloride, and the resulting mixture was refluxed for 10 hours. After the reaction, the ethanol was removed under reduced pressure, and the residue was dissolved in chloroform. The resulting solution was washed with a 5% aqueous sodium hydroxide solution and water in this order. Thereafter, the chloroform layer was dried with anhydrous sodium sulfate, and then the chloroform was removed by distillation. The residue was crystallized with petroleum ether and then recrystallized from chloroform-petroleum ether to obtain 2.1 g. of 5-(1'-ethoxycarbonyl)propoxy-3,4-dihydrocarbostyril in the form of colorless needle-like crystals, m.p. 108°–109° C.

EXAMPLE 62

2.3 Grams of 6-(1'-carboxy)ethoxy-carbostyril and 1.5 g. of cyclohexanol were added to 50 ml. of benzene, and the resulting mixture was refluxed for 15 hours by use of a Dean Stark apparatus (while removing the formed water out of the system). After the reaction, the solvent was removed by distillation, and the residue was dissolved in chloroform. The resulting solution was washed with a 5% aqueous sodium hydrogen carbonate solution and water in this order, and the chloroform layer was dried with anhydrous sodium sulfate. Subsequently, the chloroform was removed by distillation, and the residue was crystallized with petroleum ether and then recrystallized from chloroform-petroleum ether to obtain 2.2 g. of 6-(1'-cyclohexyloxycarbonyl)ethoxy-carbostyril in the form of colorless needle-like crystals, m.p. 162°–163° C.

EXAMPLE 63

2.5 Grams of 7-(1'-carboxy)propoxy-3,4-dihydrocarbostyril was added little by little to a solution of 2 g. of thionyl chloride in 20 ml. of n-amyl alcohol with stirring and while externally cooling with ice, and the resulting mixture was stirred at said temperature for 30 minutes. After the reaction, the reaction liquid was poured into 200 ml. of ethyl acetate, washed with an ethyl acetate solution, a 5% aqueous sodium hydroxide solution and water in this order and then dried with anhydrous sodium sulfate. Subsequently, the ethyl acetate was removed by distillation, and the residue was crystallized with petroleum ether and then recrystallized from chloroform-petroleum ether to obtain 2.2 g. of 7-(1'-n-amyloxycarbonyl)propoxy-3,4-dihydrocarbostyril in the form of colorless needle-like crystals, m.p. 78°–80° C.

EXAMPLES 64–129

According to Example 61, such compounds as shown in Tables 8 and 9 were obtained.

Table 8

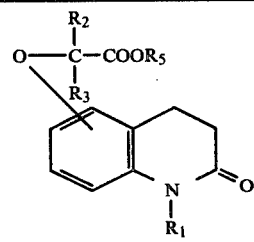

| Example No. | Position of substituent | $R_1$ | $R_2$ | $R_3$ | $R_5$ | Crystal form | M.P. (B.P.) °C. |
|---|---|---|---|---|---|---|---|
| 64 | 5 | H | H | H | $CH_3$ | Colorless needle-like crystals | 179–180 |
| 65 | 5 | H | H | H | $n\text{-}C_5H_{11}$ | " | 144–145 |
| 66 | 5 | H | H | H | $CH_2\text{-}\phi$ | " | 163–164 |
| 67 | 5 | H | H | H | (cyclohexyl) | " | 162–163 |
| 68 | 5 | H | $CH_3$ | H | $CH_3$ | " | 137–138 |
| 69 | 5 | H | $CH_3$ | H | $n\text{-}C_3H_7$ | " | 111–112 |
| 70 | 5 | H | $CH_3$ | H | $iso\text{-}C_3H_7$ | " | 134–135 |
| 71 | 5 | H | $CH_3$ | H | $n\text{-}C_4H_9$ | " | 103–104 |
| 72 | 5 | H | $CH_3$ | H | $n\text{-}C_5H_{11}$ | " | 102–103 |
| 73 | 5 | H | $CH_3$ | H | $i\text{-}C_5H_{11}$ | " | 107–108 |
| 74 | 5 | H | $CH_3$ | H | $CH_2\text{-}\phi$ | " | 132–134 |
| 75 | 5 | H | $CH_3$ | H | (cyclohexyl) | " | 116–117 |
| 76 | 5 | H | $C_2H_5$ | H | $i\text{-}C_3H_7$ | " | 120–121 |
| 77 | 5 | H | $C_2H_5$ | H | n-Butyl | " | 77–78 |
| 78 | 5 | H | $C_2H_5$ | H | $i\text{-}C_5H_{11}$ | " | 92–93 |
| 79 | 5 | H | $C_2H_5$ | H | $CH_2\text{-}\phi$ | " | 109–110 |
| 80 | 5 | H | $C_2H_5$ | H | (cyclohexyl) | " | 123–124 |
| 81 | 5 | $CH_3$ | $CH_3$ | H | $C_2H_5$ | " | 44–45 |
| 82 | 5 | $CH_2\text{-}\phi$ | $CH_3$ | H | $C_2H_5$ | " | 75–78 |
| 83 | 5 | $CH_2\text{-}CH=CH_2$ | $CH_3$ | H | $C_2H_5$ | Colorless oil | (bp$_{0.5}$ 157–158) |
| 84 | 5 | $CH_3$ | $C_2H_5$ | H | $C_2H_5$ | " | (bp$_{0.6}$ 160–162) |
| 85 | 5 | $CH_2\text{-}\phi$ | $CH_3$ | H | $n\text{-}C_5H_{11}$ | " | (bp$_{0.6}$ 211–213) |
| 86 | 6 | H | H | H | $CH_3$ | Colorless needle-like crystals | 155–156 |
| 87 | 6 | H | H | H | $n\text{-}C_4H_9$ | " | 118–119 |
| 88 | 6 | H | H | H | $i\text{-}C_5H_{11}$ | " | 77–78 |
| 89 | 6 | H | H | H | $CH_2\text{-}\phi$ | " | 151–152 |
| 90 | 6 | H | $CH_3$ | H | $CH_3$ | " | 139–140 |
| 91 | 6 | H | $CH_3$ | H | $i\text{-}C_3H_7$ | " | 125–126 |
| 92 | 6 | H | $CH_3$ | H | $n\text{-}C_4H_9$ | " | 102–103 |
| 93 | 6 | H | $CH_3$ | H | $n\text{-}C_5H_{11}$ | " | 88–89 |

Table 8-continued

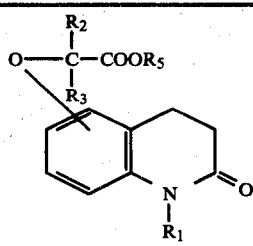

| Example No. | Position of substituent | $R_1$ | $R_2$ | $R_3$ | $R_5$ | Crystal form | M.P. (B.P.) °C. |
|---|---|---|---|---|---|---|---|
| 94 | 6 | H | $CH_3$ | H | $CH(CH_2CH_3)(CH_2CH_2CH_3)$ | Colorless plate-like crystals | 95–96 |
| 95 | 6 | H | $CH_3$ | H | cyclohexyl | Colorless needle-like crystals | 121–122 |
| 96 | 6 | H | $CH_3$ | H | $CH_2$-phenyl | Colorless plate-like crystals | 152–153 |
| 97 | 6 | H | $C_2H_5$ | H | $C_2H_5$ | " | 86–87 |
| 98 | 6 | H | $C_2H_5$ | H | $n-C_3H_7$ | Colorless needle-like crystals | 100–101 |
| 99 | 6 | H | $C_2H_5$ | H | $i-C_3H_7$ | " | 112–113 |
| 100 | 6 | $CH_3$ | $CH_3$ | H | $C_2H_5$ | Colorless oil | (bp$_{0.65}$ 170–172) |
| 101 | 6 | $CH_3$ | $C_2H_5$ | H | $C_2H_5$ | " | (bp$_{0.6}$ 160–162) |
| 102 | 6 | $CH_2$-phenyl | $CH_3$ | H | $C_2H_5$ | " | (bp$_{0.8}$ 185–188) |
| 103 | 7 | H | $CH_3$ | H | $C_2H_5$ | Colorless needle-like crystals | 85–86 |
| 104 | 7 | H | $CH_3$ | $CH_3$ | $CH_2$-phenyl | " | 98–99 |
| 105 | 7 | H | $C_2H_5$ | H | $C_2H_5$ | Colorless plate-like crystals | 83–85 |
| 106 | 7 | $C_2H_5$ | $C_2H_5$ | H | $C_2H_5$ | Colorless oil | (bp$_2$ 188–190) |
| 107 | 8 | H | $CH_3$ | H | $CH_3$ | Colorless plate-like crystals | 103–104 |
| 108 | 8 | H | $C_2H_5$ | H | $C_2H_5$ | Colorless needle-like crystals | 71–72 |
| 109 | 8 | $CH_2$-phenyl | $C_2H_5$ | H | $CH_2$-phenyl | " | 99–101 |

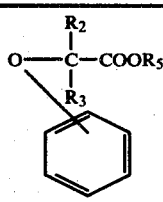

| example No. | Position of substituent | $R_1$ | $R_2$ | $R_3$ | $R_5$ | Crystal form | M.p. (B.p.) °C. |
|---|---|---|---|---|---|---|---|
| 110 | 5 | H | H | H | $CH_3$ | Colorless needle-like crystals | 256–258 |
| 111 | 5 | H | $CH_3$ | H | $CH_3$ | Colorless needle-like crystals | 196–198 |
| 112 | 5 | H | $CH_3$ | H | $n-C_3H_7$ | Colorless needle-like crystals | 153–154 |
| 113 | 5 | H | $CH_3$ | H | $i-C_3H_7$ | Colorless needle-like crystals | 182–183 |
| 114 | 5 | H | $CH_3$ | H | $n-C_5H_{11}$ | Colorless needle-like crystals | 151–152 |
| 115 | 5 | H | $CH_3$ | H | cyclohexyl | Colorless needle-like crystals | 176–177 |
| 116 | 5 | H | $CH_3$ | H | $CH_2$-phenyl | Colorless needle-like crystals | 182–183 |
| 117 | 5 | H | $C_2H_5$ | H | $C_2H_5$ | Colorless needle- | 147–149 |

-continued

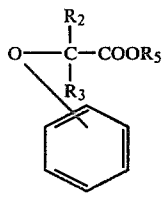

| example No. | Position of substituent | $R_1$ | $R_2$ | $R_3$ | $R_5$ | Crystal form | M.p. (B.p.) °C |
|---|---|---|---|---|---|---|---|
| 118 | 5 | H | $C_2H_5$ | H | $n\text{-}C_4H_9$ | Colorless needle-like crystals | 144–145 |
| 119 | 5 | $CH_3$ | $CH_3$ | H | $C_2H_5$ | Colorless needle-like crystals | 69–71 |
| 120 | 5 | $C_2H_5$ | $CH_3$ | H | $C_2H_5$ | Colorless oil | (bp$_{0.8}$ 185–187) |
| 121 | 6 | H | H | H | $CH_3$ | Colorless needle-like crystals | 204–206 |
| 122 | 6 | H | $CH_3$ | H | $C_2H_5$ | Colorless needle-like crystals | 159–161 |
| 123 | 6 | H | $CH_3$ | H | $n\text{-}C_4H_9$ | Colorless needle-like crystals | 136–137 |
| 124 | 6 | H | $C_2H_5$ | H | $C_2H_5$ | Colorless needle-like crystals | 1291–130 |
| 125 | 6 | H | $C_2H_5$ | H | $n\text{-}C_3H_7$ | Colorless needle-like crystals | 120–122 |
| 126 | 7 | H | $CH_3$ | $CH_3$ | $C_2H_5$ | Colorless needle-like crystals | 137–140 |
| 127 | 7 | $C_2H_5$ | $C_2H_5$ | H | $C_2H_5$ | Colorless oil | (bp$_{0.4}$ 183–184) |
| 128 | 8 | H | H | H | $C_2H_5$ | Colorless needle-like crystals | 119–120 |
| 129 | 8 | H | $CH_3$ | $CH_3$ | $C_2H_5$ | Colorless needle-like crystals | 126–128 |

EXAMPLE 130

4.0 Grams of 5-(4'-carboxy)butoxy-3,4-dihydrocarbostyril and 40 mg. of p-toluenesulfonic acid were added to 40 ml. of n-propanol, and the resulting mixture was refluxed for 10.5 hours. After cooling, the reaction liquid was charged with 50 ml. of chloroform and 50 ml. of a 5% aqueous sodium hydroxide solution and then subjected to shaking. Thereafter, the organic layer was separated, washed with a 5% aqueous sodium hydroxide solution and water in this order, and then dried with anhydrous sodium sulfate. Subsequently, the solvent was removed by distillation, and the residue was recrystallized from methanol to obtain 4.0 g. of 5-(4'-propoxycarbonyl)butoxy-3,4-dihydrocarbostyril in the form of colorless needle-like crystals, m.p. 94°–96° C.

EXAMPLE 131

2.7 Grams of 5-(3'-carboxy)propoxy-N-ethyl-3,4-dihydrocarbostyril, 20 mg. of p-toluenesulfonic acid and 0.9 g. of n-amyl alcohol was added to 27 ml. of purified benzene, and the resulting mixture was refluxed with stirring for 13.5 hours by use of a Dean Stark means. Thereafter, the solvent was removed by distillation, and the residue was charged with 50 ml. of chloroform and 50 ml. of a 5% aqueous sodium hydroxide solution and then subjected to shaking. The organic layer was separated and washed with a 5% aqueous sodium hydroxide solution and water in this order. Subsequently, the solvent was removed by distillation, and the residue was subjected to fractional distillation to obtain 3.1 g. of 5-(3'-amyloxycarbonyl)propoxy-N-ethyl-3,4-dihydrocarbostyril in the form of a colorless oil, b.p.$_{0.5}$ 202°–204° C.

EXAMPLE 132

4.2 Grams of 6-(6'-carboxy)hexyloxy-3,4-dihydrocarbostyril, 40 mg. of p-toluenesulfonic acid and 1.6 g. of benzyl alcohol were added to 42 ml. of purified benzene, and the resulting mixture was refluxed for 15 hours by use of a Dean Stark means. After the reaction, the reaction liquid was treated in the same manner as in Example 131, and the residue was recrystallized from methanol to obtain 4.8 g. of 6-(6'-benzyloxycarbonyl)-hexyloxy-3,4-dihydrocarbostyril in the form of colorless needle-like crystals, m.p. 98°–100° C.

EXAMPLES 133–175

According to Example 130, such compounds as shown in Tables 10 and 11 were obtained.

Table 10

$$O(CH_2)_mC(CH_2)_nCOOR_5$$ with $R_2$, $R_3$ substituents on quinolin-2(1H)-one ring (N-$R_1$)

| Example No. | Position of substituent | $R_1$ | $(CH_2)_m\overset{R_2}{\underset{R_3}{C}}(CH_2)_n$ | $R_5$ | Crystal form | M.p. (B.p.) °C |
|---|---|---|---|---|---|---|
| 133 | 5 | H | $(CH_2)_3$ | $C_2H_5$ | Colorless needlelike crystals | 171–173 |
| 134 | 5 | H | $(CH_2)_4$ | $n-C_3H_7$ | Colorless needlelike crystals | 130–131 |
| 135 | 5 | H | $(CH_2)_4$ | $i-C_5H_{11}$ | Colorless needlelike crystals | 134–136 |
| 136 | 5 | H | $(CH_2)_6$ | $C_2H_5$ | Colorless needlelike crystals | 138–139 |
| 137 | 5 | H | $(CH_2)_6$ | $CH_2C_6H_5$ | Colorless needlelike crystals | 111–112 |
| 138 | 5 | $C_2H_5$ | $(CH_2)_3$ | $C_2H_5$ | Colorless Oil | (191–193/0.55) |
| 139 | 5 | H | $\underset{CH_2CHCH_2}{\overset{CH_3}{\mid}}$ | $C_2H_5$ | Colorless needlelike crystals | 148–149 |
| 140 | 6 | H | $(CH_2)_3$ | $C_2H_5$ | Colorless needlelike crystals | 130–132 |
| 141 | 6 | H | $(CH_2)_3$ | $n-C_5H_{11}$ | Colorless needlelike crystals | 96–97 |
| 142 | 6 | H | $(CH_2)_6$ | $C_2H_5$ | Colorless needlelike crystals | 129–130 |
| 143 | 6 | H | $(CH_2)_6$ | $CH_2C_6H_5$ | Colorless needlelike crystals | 141–143 |
| 144 | 6 | $CH_3$ | $(CH_2)_3$ | $C_2H_5$ | Colorless needlelike crystals | 89–90 |

Table 11

$$O(CH_2)_mC(CH_2)_nCOOR_5$$ with $R_2$, $R_3$ substituents on 3,4-dihydroquinolin-2(1H)-one ring (N-$R_1$)

| Example No. | Position of substituent | $R_1$ | $(CH_2)_m\overset{R_2}{\underset{R_3}{CH}}(CH_2)_n$ | $R_5$ | Crystal form | M.p. (B.p.) °C |
|---|---|---|---|---|---|---|
| 145 | 5 | H | $(CH_2)_3$ | $C_2H_5$ | Colorless needlelike crystals | 114–116 |
| 146 | 5 | H | $(CH_2)_3$ | $i-C_3H_7$ | " | 128–130 |
| 147 | 5 | H | $(CH_2)_3$ | $n-C_5H_{11}$ | " | 112–114 |
| 148 | 5 | H | $(CH_2)_3$ | cyclohexyl | " | 122–124 |
| 149 | 5 | H | $(CH_2)_4$ | $C_2H_5$ | " | 118–120 |
| 150 | 5 | H | $(CH_2)_4$ | $i-C_5H_{11}$ | " | 96–98 |
| 151 | 5 | H | $(CH_2)_6$ | $C_2H_5$ | " | 98–100 |
| 152 | 5 | H | $(CH_2)_6$ | $n-C_4H_9$ | " | 79–81 |
| 153 | 5 | H | $(CH_2)_6$ | $CH_2C_6H_5$ | " | 84–86 |
| 154 | 5 | H | $(CH_2)_{10}$ | $C_2H_5$ | " | 97–99 |
| 155 | 5 | H | $\underset{CH_2CHCH_2}{\overset{CH_3}{\mid}}$ | $C_2H_5$ | " | 95–97 |
| 156 | 5 | H | $\underset{CH_2-CH-CH_2}{\overset{CH_3}{\mid}}$ | $n-C_4H_9$ | " | 84–85 |
| 157 | 5 | $C_2H_5$ | $(CH_2)_3$ | $C_2H_5$ | Colorless oil | (189–191/0.9) |
| 158 | 5 | $CH_2CH=CH_2$ | $(CH_2)_3$ | $i-C_3H_7$ | " | (185–187/0.8) |
| 159 | 5 | $CH_2-C_6H_5$ | $(CH_2)_6$ | $n-C_4H_9$ | Colorless needlelike crystals | 46–48 |
| 160 | 6 | H | $(CH_2)_2$ | $C_2H_5$ | " | 136–137 |
| 161 | 6 | H | $(CH_2)_3$ | $C_2H_5$ | " | 113–115 |
| 162 | 6 | H | $(CH_2)_3$ | $i-C_3H_7$ | " | 104–105 |
| 163 | 6 | H | $(CH_2)_3$ | $n-C_5H_{11}$ | " | 75–77 |
| 164 | 6 | H | $(CH_2)_4$ | $C_2H_5$ | " | 115–118 |
| 165 | 6 | H | $(CH_2)_4$ | $n-C_5H_{11}$ | " | 72–74 |
| 166 | 6 | H | $(CH_2)_6$ | $C_2H_5$ | " | 103–105 |
| 167 | 6 | H | $(CH_2)_{10}$ | $C_2H_5$ | " | 99–102 |

Table 11-continued

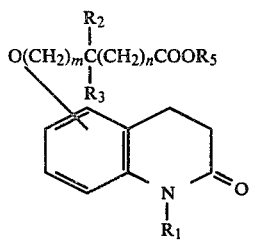

| Example No. | Position of substituent | $R_1$ | $(CH_2)_m\overset{R_2}{\underset{R_3}{CH}}(CH_2)_n$ | $R_5$ | Properties Crystal form | M.p. (B.p.) °C. |
|---|---|---|---|---|---|---|
| 168 | 6 | H | $\underset{CH_2-CH-CH_2}{CH_3}$ | $C_2H_5$ | " | 59–61 |
| 169 | 6 | H | $\underset{CH_2-CH-CH_2}{CH_3}$ | $CH_2-\phi$ | " | 63–64 |
| 170 | 6 | H | $\underset{CH_2CH_2CH}{CH_3}$ | $C_2H_5$ | Colorless oil | (206–208/0.6) |
| 171 | 6 | $CH_3$ | $(CH_2)_3$ | $C_2H_5$ | " | (197–199/0.7) |
| 172 | 7 | H | $(CH_2)_5$ | $C_2H_5$ | Colorless needlelike crystals | 71–72 |
| 173 | 7 | H | $(CH_2)_5$ | $n\text{-}C_4H_9$ | " | 82–84 |
| 174 | 8 | H | $(CH_2)_2$ | $n\text{-}C_3H_7$ | Colorless flakelike crystals | 86–87 |
| 175 | 8 | H | $(CH_2)_6$ | $n\text{-}C_3H_7$ | Colorless oil | (213–214/0.6) |

EXAMPLE 176

To 2.5 g. of 5-ethoxycarbonylmethoxy-3,4-dihydrocarbostyril was added 8 ml. of ammonia water, and the resulting mixture was stirred at room temperature for 1.5 hours to deposit crystals. The deposited crystals were recovered by filtration and then recrystallized from methanol to obtain 1.5 g. of a substance in the form of colorless needle-like crystals, m.p. 293°–297° C. According to NMR, IR and elementary analysis, it was confirmed that the said substance was 5-carbamoylmethoxy-3,4-dihydrocarbostyril.

EXAMPLE 177

To 2 g. of 5-ethoxycarbonylmethoxy-3,4-dihydrocarbostyril were added 6.8 ml. of isopropylamine and 10 ml. of water, and the resulting mixture was stirred at room temperature for 2 hours to deposit crystals. The deposited crystals were recovered by filtration and then recrystallized from ethanol to obtain 0.5 g. of a substance in the form of colorless needle-like crystals, m.p. 208.5°–209.5° C. According to NMR, IR and elementary analysis, it was confirmed that the said substance was 5-(N-isopropylcarbamoyl)methoxy-3,4-dihydrocarbostyril.

EXAMPLE 178

To 2 g. of 5-ethoxycarbonylmethoxy-3,4-dihydrocarbostyril were added 10 ml. of piperidine and 10 ml. of water, and the resulting mixture was stirred at room temperature for 2 hours. Thereafter, the reaction liquid was concentrated to dryness, and the concentrate was dissolved in chloroform. The resulting solution was washed with water and then dried with anhydrous sodium sulfate, and the chloroform was removed by distillation. The residue was recrystallized from ligroin-ethanol to obtain 0.3 g. of a substance in the form of colorless needle-like crystals, m.p. 179°–180.5° C. According to NMR, IR and elementary analysis, it was confirmed that the said substance was 5-(1'-piperidinocarbonyl)methoxy-3,4-dihydrocarbostyril.

EXAMPLE 179

To 2 g. of 5-ethoxycarbonylmethoxy-3,4-dihydrocarbostyril were added 6.9 ml. of morpholine and 10 ml. of water, and the resulting mixture was stirred at room temperature for 5 hours to deposit crystals. The deposited crystals were recovered by filtration and then recrystallized from ethanol to obtain 0.3 g. of a substance in the form of colorless needle-like crystals, m.p. 217°–218.5° C. According to NMR, IR and elementary analysis, it was confirmed that the said substance was 5-(1'-morpholinocarbonyl)-methoxy-3,4-dihydrocarbostyril.

EXAMPLE 180

To 2 g. of 5-ethoxycarbonylmethoxy-3,4-dihydrocarbostyril were added 8.7 ml. of benzylamine and 13 ml. of water, and the resulting mixture was stirred at room temperature to deposit crystals. The deposited crystals were recovered by filtration and then recrystallized from ethanol to obtain 1.9 g. of a substance in the form of colorless needle-like crystals, m.p. 242°–243° C. According to NMR, IR and elementary analysis, it was confirmed that the said substance was 5-(N-benzylcarbamoyl)methoxy-3,4-dihydrocarbostyril.

EXAMPLES 181–187

According to Example 176, such compounds as shown in Table 12 were obtained.

Table 12

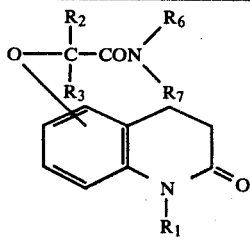

| Example No. | Position of substituent | R₁ | R₂ | R₃ | R₆ | R₇ | Properties Crystal form | m.p. (°C.) |
|---|---|---|---|---|---|---|---|---|
| 181 | 6 | H | H | H | H | H | Colorless needle-like crystals | 244–246.5 |
| 182 | 7 | H | H | H | H | H | Colorless needle-like crystals | 218–219 |
| 183 | 8 | H | H | H | H | H | Colorless needle-like crystals | 244–245.5 |
| 184 | 5 | CH₃ | H | H | H | H | Colorless needle-like crystals | 246–247.5 |
| 185 | 5 | H | CH₃ | H | H | H | Colorless amorphous solid | 268–269 |
| 186 | 5 | H | CH₃ | CH₃ | H | H | Colorless prism-like crystals | 216–222.5 |
| 187 | 5 | H | H | H | CH₃ | CH₃ | Colorless needle-like crystals | 184–186 |

EXAMPLE 188

To 2.6 g. of N-ethyl-5-(3'-ethoxycarbonyl)-propoxy-3,4-dihydrocarbostyril were added 10.5 ml of benzylamine and 10 ml. of water, and the resulting mixture was stirred at room temperature for 2 hours to deposit crystals. The deposited crystals were recovered by filtration and then recrystallized from ethanol to obtain 1.9 g. of N-ethyl-5-(3'-benzylcarbamoyl)propoxy-3,4-dihydrocarbostyril in the form of colorless amorphous solid, m.p. 131°–134° C.

EXAMPLE 189

To 2.6 g. of 8-(4'-ethoxycarbonyl)butoxycarbostyril was added 8 ml. of aqueous ammonia, and the resulting mixture was stirred at room temperature for 1.5 hours to deposit crystals. The deposited crystals were recovered by filtration and then recrystallized from methanol to obtain 2.1 g of 8-(4'-carbamoyl)butoxycarbostyril in the form of colorless needle-like crystals, m.p. 178°–180° C.

According to Example 188, the following compounds were obtained.

EXAMPLE 190

6-[3'-(N-n-Propylcarbamoyl)-2'-methylpropoxy]-3,4-dihydrocarbostyril, colorless amorphous solid, m.p. 149°–150° C.

EXAMPLE 191

5-(3'-Carbamoyl)propoxycarbostyril, colorless needle-like crystals, m.p. 252°–255° C.

EXAMPLE 192

5 Grams of anhydrous hydrogen chloride was injected over a period of about 4 hours into a solution comprising 6 g. of anhydrous ethanol, 300 ml. of anhydrous ether and 25 g. of 5-(4'-cyano(butoxy-3,4-dihydrocarbostyril with stirring and while maintaining the temperature at −10° to −5° C. by externally cooling with ice-methanol. This solution was stirred at said temperature for 20 hours and then poured into 50 ml. of 20% hydrochloric acid while maintaining the temperature at 30° to 40° C. After stirring at 30° to 40° C. for 10 minutes, the solution was extracted with ethyl acetate, and the ethyl acetate layer was washed with water, saturated sodium bicarbonate water and water in this order and then dried with anhydrous sodium sulfate. Subsequently, the solvent was removed, and the residue was recrystallized from methanol to obtain 12 g. of 5-(4'-ethoxycarbonyl)butoxy-3,4-dihydrocarbostyril in the form of colorless needle-like crystals, m.p. 118°–120° C.

EXAMPLE 193

5 Grams of anhydrous hydrogen chloride was injected over a period of about 5 hours into a solution comprising 7 g. of anhydrous ethanol, 300 ml. of anhydrous ether and 26 g. of N-ethyl-5-(3'-cyano)-propoxy-3,4-dihydrocarbostyril with stirring and while maintaining the temperature at −10° to −5° C. by externally cooling with ice-methanol. This solution was stirred at said temperature for 15 hours and then poured into 50 ml. of 20% hydrochloric acid while maintaining the temperature at 30° to 40° C. After stirring at said temperature for 10 minutes, the solution was extracted with ethyl acetate, and the ethyl acetate layer was washed with water, saturated sodium bicarbonate water and water in this order and then dried with anhydrous sodium sulfate. Subsequently, the solvent was removed, and the residue was subjected to distillation under reduced pressure to obtain 15 g. of N-ethyl-5-(3'-ethoxycarbonyl)propoxy-3,4-dihydrocarbostyril in the form of a colorless liquid, b.p.$_{0.9}$ 189°–191° C.

EXAMPLES 194–259

According to Examples 193, such compounds as shown in Tables 13 and 14 were obtained.

Table 13

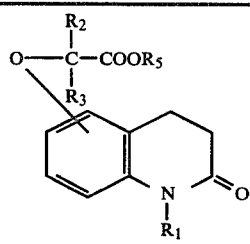

| Example No. | Position of substituent | R$_1$ | R$_2$ | R$_3$ | R$_5$ | Crystal form | M.p. (B.p.) °C. |
|---|---|---|---|---|---|---|---|
| 194 | 5 | H | H | H | C$_2$H$_5$ | Colorless needle-like crystals | 146–148 |
| 195 | 5 | H | CH$_3$ | H | C$_2$H$_5$ | Colorless needle-like crystals | 114–118 |
| 196 | 5 | H | CH$_3$ | CH$_3$ | C$_2$H$_5$ | Colorless needle-like crystals | 121.5–122.5 |
| 197 | 5 | CH$_3$ | H | H | C$_2$H$_5$ | Colorless needle-like crystals | 64.5–66.5 |
| 198 | 6 | H | H | H | C$_2$H$_5$ | Colorless needle-like crystals | 129–132.5 |
| 199 | 6 | H | CH$_3$ | H | C$_2$H$_5$ | Colorless needle-like crystals | 111–113 |
| 200 | 6 | H | CH$_3$ | CH$_3$ | C$_2$H$_5$ | Colorless needle-like crystals | 72–73.5 |
| 201 | 7 | H | H | H | C$_2$H$_5$ | Colorless needle-like crystals | 106–107 |
| 202 | 7 | H | CH$_3$ | CH$_3$ | C$_2$H$_5$ | Colorless needle-like crystals | 114–115.5 |
| 203 | 8 | H | H | H | C$_2$H$_5$ | Colorless needle-like crystals | 92.5–94 |
| 204 | 8 | H | CH$_3$ | H | C$_2$H$_5$ | Colorless needle-like crystals | 94–99 |
| 205 | 8 | H | CH$_3$ | CH$_3$ | C$_2$H$_5$ | Colorless needle-like crystals | 125–126.5 |
| 206 | 5 | H | H | H | CH$_3$ | Colorless needle-like crystals | 179–180 |
| 207 | 5 | H | H | H | n-C$_5$H$_{11}$ | Colorless needle-like crystals | 144–145 |
| 208 | 5 | H | H | H | CH$_2$–C$_6$H$_5$ | Colorless needle-like crystals | 163–164 |
| 209 | 5 | H | H | H | cyclohexyl | Colorless needle-like crystals | 162–163 |
| 210 | 5 | H | CH$_3$ | H | CH$_3$ | Colorless needle-like crystals | 137–138 |
| 211 | 5 | H | H | H | n-C$_3$H$_7$ | Colorless needle-like crystals | 111–112 |
| 212 | 5 | H | H | H | iso-C$_3$H$_7$ | Colorless needle-like crystals | 134–135 |
| 213 | 5 | H | H | H | n-C$_4$H$_9$ | Colorless needle-like crystals | 103–104 |
| 214 | 5 | H | H | H | n-C$_5$H$_{11}$ | Colorless neddle-like crystals | 102–103 |
| 215 | 5 | H | H | H | iso-C$_5$H$_{11}$ | Colorless needle-like crystals | 107–108 |
| 216 | 5 | H | H | H | CH$_2$–C$_6$H$_5$ | Colorless needle-like crystals | 132–134 |
| 217 | 5 | H | H | H | cyclohexyl | Colorless needle-like crystals | 116–117 |
| 218 | 5 | H | C$_2$H$_5$ | H | C$_2$H$_5$ | Colorless needle-like crystals | 108–109 |
| 219 | 5 | H | C$_2$H$_5$ | H | iso-C$_3$H$_7$ | Colorless needle-like crystals | 120–121 |
| 220 | 5 | H | C$_2$H$_5$ | H | n-C$_4$H$_9$ | Colorless needle-like crystals | 77–78 |
| 221 | 5 | H | C$_2$H$_5$ | H | iso-C$_5$H$_{11}$ | Colorless needle-like crystals | 92–93 |

Table 13-continued

Structure: quinolin-2(1H)-one with substituent O—C(R2)(R3)—COOR5 on the benzene ring, and R1 on N.

| Example No. | Position of substituent | R1 | R2 | R3 | R5 | Crystal form | M.p. (B.p.) °C |
|---|---|---|---|---|---|---|---|
| 222 | 5 | H | $C_2H_5$ | H | $CH_2$—C6H5 (benzyl) | Colorless needle-like crystals | 109–110 |
| 223 | 5 | H | $C_2H_5$ | H | cyclohexyl | Colorless needle-like crystals | 123–124 |
| 224 | 5 | $CH_3$ | $CH_3$ | H | $C_2H_5$ | Colorless needle-like crystals | 44–45 |
| 225 | 5 | $CH_2$—C6H5 | $CH_3$ | H | $C_2H_5$ | Colorless needle-like crystals | 75–78 |
| 226 | 5 | $CH_2$—CH=$CH_2$ | $CH_3$ | H | $C_2H_5$ | Colorless oil | (bp$_{0.5}$ 157–158) |
| 227 | 5 | $CH_3$ | $C_2H_5$ | H | $C_2H_5$ | " | (bp$_{0.6}$ 160–162) |
| 228 | 5 | $CH_2$—C6H5 | $CH_3$ | H | n-$C_5H_{11}$ | Oil | (bp$_{0.6}$ 211–213) |
| 229 | 6 | H | H | H | $CH_3$ | Colorless needle-like crystals | 155–156 |
| 230 | 6 | H | H | H | n-$C_4H_9$ | Colorless needle-like crystals | 118–119 |
| 231 | 6 | H | H | H | iso-$C_5H_{11}$ | Colorless needle-like crystals | 77–78 |
| 232 | 6 | H | H | H | $CH_2$—C6H5 | Colorless needle-like crystals | 151–152 |
| 233 | 6 | H | $CH_3$ | H | $CH_3$ | Colorless needle-like crystals | 139–140 |
| 234 | 6 | H | $CH_3$ | H | iso-$C_3H_7$ | Colorless needle-like crystals | 125–126 |
| 235 | 6 | H | $CH_3$ | H | n-$C_4H_9$ | Colorless needle-like crystals | 102–103 |
| 236 | 6 | H | $CH_3$ | H | n-$C_5H_{11}$ | Colorless needle-like crystals | 88–89 |
| 237 | 6 | H | $CH_3$ | H | CH($CH_2CH_3$)($CH_2CH_2CH_3$) | Colorless plate-like crystals | 95–96 |
| 238 | 6 | H | $CH_3$ | H | cyclohexyl | Colorless needle-like crystals | 121–122 |
| 239 | 6 | H | $CH_3$ | H | $CH_2$—C6H5 | Colorless plate-like crystals | 152–153 |
| 240 | 6 | H | $C_2H_5$ | H | $C_2H_5$ | Colorless plate-like crystals | 86–87 |
| 241 | 6 | H | $C_2H_5$ | H | n-$C_3H_7$ | Colorless needle-like crystals | 100–101 |
| 242 | 6 | H | $C_2H_5$ | H | iso-$C_3H_7$ | Colorless needle-like crystals | 112–113 |
| 243 | 6 | $CH_3$ | $CH_3$ | H | $C_2H_5$ | Colorless oil | (bp$_{0.65}$ 170–172) |
| 244 | 6 | $CH_3$ | $C_2H_5$ | H | $C_2H_5$ | " | (bp$_{0.6}$ 160–162) |

Table 13-continued

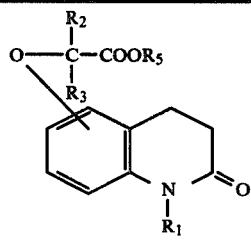

| Example No. | Position of substituent | R1 | R2 | R3 | R5 | Crystal form | M.p. (B.p.) °C. |
|---|---|---|---|---|---|---|---|
| 245 | 6 | CH2-phenyl | CH3 | H | C2H5 | " | (bp$_{1.8}$ 185–188) |
| 246 | 7 | H | CH3 | H | C2H5 | Colorless needle-like crystals | 85–86 |
| 247 | 7 | H | CH3 | CH3 | CH2-phenyl | Colorless needle-like crystals | 98–99 |
| 248 | 7 | H | C2H5 | H | C2H5 | Colorless plate-like crystals | 83–85 |
| 249 | 7 | H | C2H5 | H | n-C5H11 | Colorless needle-like crystals | 78–80 |
| 250 | 7 | C2H5 | C2H5 | H | C2H5 | Colorless oil | (bp$_{2.0}$ 188–190) |
| 251 | 8 | H | CH3 | H | CH3 | Colorless plate-like crystals | 103–104 |
| 252 | 8 | H | C2H5 | H | C2H5 | Colorless needle-like crystals | 71–72 |
| 253 | 8 | CH2-phenyl | C2H5 | H | CH2-phenyl | Colorless needle-like crystals | 99–101 |

Table 14

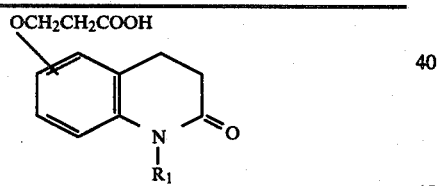

| Example No. | Position of substituent | R1 | Crystal form | M.p. °C. |
|---|---|---|---|---|
| 254 | 5 | H | Colorless needle-like crystals | 221–224 |
| 255 | 5 | CH2CH2COOH | Colorless needle-like crystals | 222.5–224 |
| 256 | 6 | H | Colorless needle-like crystals | 188–190.5 |
| 257 | 6 | CH2CH2COOH | Colorless needle-like crystals | 167–169 |
| 258 | 7 | H | Colorless needle-like crystals | 161–164.5 |
| 259 | 7 | CH2CH2COOH | Colorless needle-like crystal | 157–159 |

EXAMPLE 260

5 Grams of anhydrous hydrogen chloride was injected over a period of about 5 hours into a solution comprising 11 g. of anhydrous amyl alcohol, 300 ml. of anhydrous ether and 23 g. of 6-(3'-cyano)propoxy-3,4-dihydrocarbostyril with stirring and while maintaining the temperature at −10° to −5° C. by externally cooling with ice-methanol. This solution was further stirred at said temperature for 15 hours and then poured into 50 ml. of 20% hydrochloric acid while maintaining the temperature at 30° to 40° C. After stirring at said temperature for 15 minutes, the solution was extracted with ethyl acetate, and the organic layer was washed with water, saturated sodium bicarbonate water and water in this order and then dried with anhydrous sodium sulfate. Subsequently, the solvent was removed under reduced pressure, and the residue was recrystallized from ethanol to obtain 14 g. of 6-(3'-amyloxycarbonyl)-propoxy-3,4-dihydrocarbostyril in the form of colorless needle-like crystals, m.p. 75°–77° C.

EXAMPLES 261–303

According to Examples 192, such compounds as shown in Tables 15 and 16 were obtained.

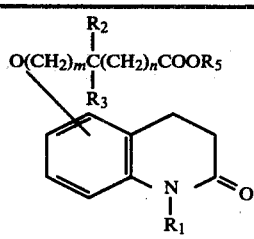

| Example No. | Position of substituent | R₁ | (CH$_2$)$_m$C(R$_2$)(R$_3$)(CH$_2$)$_n$ | R₅ | Crystal form | M.p. (B.p.) °C |
|---|---|---|---|---|---|---|
| 261 | 5 | H | (CH$_2$)$_3$ | C$_2$H$_5$ | Colorless needle-like crystals | 114–116 |
| 262 | 5 | H | (CH$_2$)$_3$ | i-C$_3$H$_7$ | Colorless needle-like crystals | 128–130 |
| 263 | 5 | H | (CH$_2$)$_3$ | n-C$_5$H$_{11}$ | Colorless needle-like crystals | 112–114 |
| 264 | 5 | H | (CH$_2$)$_3$ | C$_6$H$_{11}$ (cyclohexyl) | Colorless needle-like crystals | 122–124 |
| 265 | 5 | H | (CH$_2$)$_4$ | n-C$_3$H$_7$ | Colorless needle-like crystals | 94–96 |
| 266 | 5 | H | (CH$_2$)$_4$ | i-C$_5$H$_{11}$ | Colorless needle-like crystals | 96–98 |
| 267 | 5 | H | (CH$_2$)$_6$ | C$_2$H$_5$ | Colorless needle-like crystals | 98–100 |
| 268 | 5 | H | (CH$_2$)$_6$ | n-C$_4$H$_9$ | Colorless needle-like crystals | 79–81 |
| 269 | 5 | H | (CH$_2$)$_6$ | CH$_2$C$_6$H$_5$ | Colorless needle-like crystals | 84–86 |
| 270 | 5 | H | (CH$_2$)$_{10}$ | C$_2$H$_5$ | Colorless needle-like crystals | 97–99 |
| 271 | 5 | H | CH$_2$CH(CH$_3$)CH$_2$ | C$_2$H$_5$ | Colorless needle-like crystals | 95–97 |
| 272 | 5 | H | CH$_2$CH(CH$_3$)CH$_2$ | n-C$_4$H$_9$ | Colorless needle-like crystals | 84–85 |
| 273 | 5 | C$_2$H$_5$ | (CH$_2$)$_3$ | n-C$_5$H$_{11}$ | Colorless oil | (202–204/0.5) |
| 274 | 5 | CH$_2$CH=CH$_2$ | (CH$_2$)$_3$ | i-C$_3$H$_7$ | Colorless oil | (185–187/0.8) |
| 275 | 5 | CH$_2$C$_6$H$_5$ | (CH$_2$)$_6$ | n-C$_4$H$_9$ | Colorless needle-like crystals | 46–48 |
| 276 | 6 | H | (CH$_2$)$_2$ | C$_2$H$_5$ | Colorless needle-like crystals | 136–137 |
| 277 | 6 | H | (CH$_2$)$_3$ | C$_2$H$_5$ | Colorless needle-like crystals | 113–115 |
| 278 | 6 | H | (CH$_2$)$_3$ | i-C$_3$H$_7$ | Colorless needle-like crystals | 104–105 |
| 279 | 6 | H | (CH$_2$)$_4$ | C$_2$H$_5$ | Colorless needle-like crystals | 115–118 |
| 280 | 6 | H | (CH$_2$)$_4$ | n-C$_5$H$_{11}$ | Colorless needle-like crystals | 72–74 |
| 281 | 6 | H | (CH$_2$)$_6$ | C$_2$H$_5$ | Colorless needle-like crystals | 103–105 |
| 282 | 6 | H | (CH$_2$)$_6$ | CH$_2$C$_6$H$_5$ | Colorless needle-like crystals | 98–100 |
| 283 | 6 | H | (CH$_2$)$_{10}$ | C$_2$H$_5$ | Colorless needle-like crystals | 99–102 |
| 284 | 6 | H | CH$_2$—CH(CH$_3$)—CH$_2$ | C$_2$H$_5$ | Colorless needle-like crystals | 59–61 |
| 285 | 6 | H | CH$_2$—CH(CH$_3$)—CH$_2$ | CH$_2$C$_6$H$_5$ | Colorless needle-like crystals | 63–64 |
| 286 | 6 | H | CH$_2$CH$_2$CH(CH$_3$) | C$_2$H$_5$ | Colorless oil | (206–208/0.6) |
| 287 | 6 | CH$_3$ | (CH$_2$)$_3$ | C$_2$H$_5$ | Colorless oil | (197–199/0.7) |
| 288 | 7 | H | (CH$_2$)$_5$ | C$_2$H$_5$ | Colorless needle-like crystals | 71–72 |
| 289 | 7 | H | (CH$_2$)$_5$ | n-C$_4$H$_9$ | Colorless needle-like crystals | 82–84 |
| 290 | 8 | H | (CH$_2$)$_2$ | n-C$_3$H$_7$ | Colorless flake-like crystals | 86–87 |

-continued

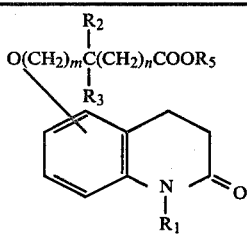

| Example No. | Position of substituent | $R_1$ | $(CH_2)_mC(CH_2)_n$ $R_3$ (with $R_2$) | $R_5$ | Properties Crystal form | M.p. (B.p.) °C. |
|---|---|---|---|---|---|---|
| 291 | 8 | H | $(CH_2)_6$ | n-$C_3H_7$ | Colorless oil | (213–214/0.6) |

Table 16

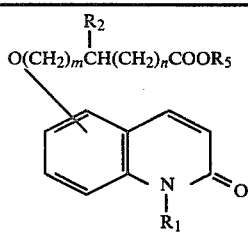

| Example No. | Position of substituent | $R_1$ | $(CH_2)_mCH(CH_2)_n$ (with $R_2$) | $R_5$ | Properties Crystal form | M.p. (B.p.) °C. |
|---|---|---|---|---|---|---|
| 292 | 5 | H | $(CH_2)_3$ | $C_2H_5$ | Colorless needle-like crystals | 171–173 |
| 293 | 5 | H | $(CH_2)_4$ | n-$C_3H_7$ | Colorless needle-like crystals | 130–131 |
| 294 | 5 | H | $(CH_2)_4$ | i-$C_5H_{11}$ | Colorless needle-like crystals | 134–136 |
| 295 | 5 | H | $(CH_2)_6$ | $C_2H_5$ | Colorless needle-like crystals | 138–139 |
| 296 | 5 | H | $(CH_2)_6$ | $CH_2C_6H_5$ | Colorless needle-like crystals | 111–112 |
| 297 | 5 | $C_2H_5$ | $(CH_2)_3$ | $C_2H_5$ | Colorless oil | (191–193/0.55) |
| 298 | 5 | H | $CH_2CHCH_2$ with $CH_3$ | $C_2H_5$ | Colorless needle-like crystals | 148–149 |
| 299 | 6 | H | $(CH_2)_3$ | $C_2H_5$ | Colorless needle-like crystals | 130–132 |
| 300 | 6 | H | $(CH_2)_3$ | n-$C_5H_{11}$ | Colorless needle-like crystals | 96–97 |
| 301 | 6 | H | $(CH_2)_6$ | $C_2H_5$ | Colorless needle-like crystals | 129–130 |
| 302 | 6 | H | $(CH_2)_6$ | $CH_2C_6H_5$ | Colorless needle-like crystals | 141–143 |
| 303 | 6 | $CH_3$ | $(CH_2)_3$ | $C_2H_5$ | Colorless needle-like crystals | 89–90 |

REFERENTIAL EXAMPLE 1

To a solution of 0.4 g. of sodium hydroxide in 20 ml. of water was added 2 g. of 6-(1'-ethoxycarbonyl)ethoxy-3,4-dihydrocarbostyril, and the resulting mixture was refluxed for 10 minutes. After cooling, the reaction liquid was charged with concentrated hydrochloric acid to deposit crystals. The deposited crystals were recovered by filtration and then recrystallized from water to obtain 1.5 g. of 6-(1'-carboxy)ethoxy-3,4-dihydrocarbostyril in the form of colorless needle-like crystals, m.p. 207°–210.5° C.

REFERENTIAL EXAMPLE 2

To a solution of 2.6 g. of 5-(1'-ethoxycarbonyl)ethoxy-3,4-dihydrocarbostyril in 30 ml. of dimethylformamide was added 300 mg. of sodium hydride, and the resulting mixture was stirred until the generation of hydrogen was complete. Thereafter, the mixture was charged with 2.8 g. of methyl iodide and then stirred at room temperature for 1 hour to deposit crystals of sodium iodide. The deposited crystals were recovered by filtration, and the dimethylformamide was removed by distillation. Subsequently, the residue was recrystallized from chloroform-petroleum ether to obtain 2.5 g. of N-methyl-5-(1'-ethoxycarbonyl)ethoxy-3,4-dihydrocarbostyril in the form of colorless needle-like crystals, m.p. 44°–45° C.

REFERENTIAL EXAMPLE 3

To a solution of 2.3 g. of N-methyl-5-(1'-carboxy)ethoxycarbostyril in 50 ml. of methanol was added 0.2 g. of palladium black, and the resulting mixture was subjected to reduction at 50° C. for 8 hours under a hydrogen pressure of 2.5 atm. Thereafter, the catalyst was removed by filtration, and the filtrate was concentrated to dryness. Subsequently, the concentrate was recrystallized from hydrous ethanol to obtain 1.8 g. of N-methyl-5-(1'-carboxy)ethoxy-3,4-dihydrocarbostyril in the form of colorless needle-like crystals, m.p. 148°–149° C.

REFERENTIAL EXAMPLE 4

To a solution of 2.5 g. of 5-(4'-n-propoxycarbonyl)-n-butoxycarbostyril in 50 ml. of methanol was added 0.1 g. of palladium black, and the resulting mixture was subjected to reduction at 50° C. for 8 hours under a hydrogen pressure of 2.5 atm. After completion of the reaction, the catalyst was removed by filtration, and the filtrate was concentrated to dryness. Subsequently, the concentrate was recrystallized from methanol to obtain 1.9 g. of 5-(4'-n-propoxycarbonyl)-n-butoxy-3,4-dihydrocarbostyril in the form of colorless needle-like crystals, m.p. 94°–96° C.

REFERENTIAL EXAMPLE 5

To 50 ml. of dioxane were added 2.6 g. of 6-(2'-ethoxycarbonyl)ethoxy-3,4-dihydrocarbostyril and 3.8 g. of 2,3-dichloro-5,6-dicyanobenzoquinone, and the resulting mixture was refluxed for 10 hours. Thereafter, the reaction liquid was cooled to deposit crystals. The deposited crystals were removed by filtration, and the filtrate was concentrated. The concentrate was dissolved in ethyl acetate, and the resulting ethyl acetate solution was washed with a 5% aqueous sodium carbonate solution and water in this order and then dried with anhydrous sodium sulfate. Subsequently, the ethyl acetate was removed, and the residue was subjected to silica gel column chromatography using ethyl acetate as development solvent. The resulting eluate was concentrated, and the concentrate was recrystallized from methanol to obtain 1.9 g. of 6-(2'-ethoxycarbonyl)ethoxycarbostyril in the form of colorless needle-like crystals, m.p. 159°–161° C.

EXAMPLE 304

A solution of 9.1 g. of sodium ethylate in 200 ml. of water was charged with 20 g. of 5-hydroxy-3,4-dihydrocarbostyril and refluxed for 2 hours. This solution was further charged with 21 g. of ethyl α-bromoacetate and refluxed for 4 hours to deposit sodium bromide, which was then removed by filtration, and the filtrate was cooled to deposit crystals. The deposited crystals were separated by filtration and then recrystallized from ethanol to obtain 20 g. of 5-ethoxycarbonylmethoxy-3,4-dihydrocarbostyril in the form of colorless needle-like crystals, m.p. 146°–148° C.

EXAMPLE 305

A solution of 3.4 g. of sodium ethylate in 100 ml. of ethanol was charged with 7.3 g. of 6-hydroxy-3,4-dihydrocarbostyril and refluxed for 2 hours. This solution was further charged with 10 g. of ethyl α-bromopropionate and refluxed for 5 hours to deposit sodium bromide, which was then removed by filtration, and the filtrate was concentrated to dryness under reduced pressure. The concentrate was dissolved in ethyl acetate, and the resulting solution was washed with a dilute aqueous sodium hydroxide solution and then dried with Glauber's salt to remove the ethyl acetate. Subsequently, the residue was recrystallized from a mixed solvent comprising water and ethanol to obtain 5 g. of 6-(1'-ethoxycarbonyl)-ethoxy-3,4-dihydrocarbostyril in the form of colorless scale-like crystals, m.p. 111°–113° C.

EXAMPLE 306

A solution of 3.4 g. of sodium ethylate in 100 ml. of ethanol was charged with 7.3 g. of 7-hydroxy-3,4-dihydrocarbostyril and refluxed for 2 hours. This solution was further charged with 10.7 g. of ethyl α-bromoisobutyrate and refluxed for 6 hours to deposit sodium bromide, which was then removed by filtration, and the filtrate was concentrated to dryness under reduced pressure. The concentrate was dissolved in chloroform, and the resulting solution was washed with a dilute aqueous sodium hydroxide solution and then dried with Glauber's salt to remove the chloroform. Subsequently, the residue was recrystallized from a mixed solvent comprising water and ethanol to obtain 5 g. of 7-(2'-ethoxycarbonyl)isopropoxy-3,4-dihydrocarbostyril in the form of colorless scale-like crystals, m.p. 114°–115.5° C.

EXAMPLE 307

A solution of 1.5 g. of sodium ethylate in 50 ml. of ethanol was charged with 3.3 g. of 8-hydroxy-3,4-dihydrocarbostyril and refluxed for 2 hours. This solution was further charged with 5 g. of ethyl α-bromoacetate and refluxed for 4 hours to deposit sodium bromide, which was then removed by filtration, and the filtrate was concentrated to dryness under reduced pressure. The concentrate was dissolved in ethyl acetate, and the resulting solution was washed with a dilute aqueous sodium hydroxide solution and then dried with anhydrous sodium sulfate to remove the ethyl acetate. Subsequently, the residue was recrystallized from ligroin to obtain 2.6 g. of 8-ethoxycarbonylmethoxy-3,4-dihydrocarbostyril in the form of colorless needle-like crystals, m.p. 92.5°–94° C.

EXAMPLES 308–315

According to Example 304, such compounds as shown in Table 17 were obtained.

Table 17

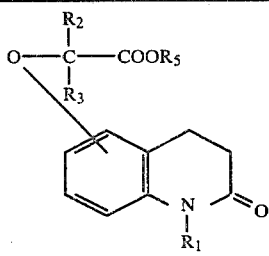

| Example No. | Position of substituent | $R_1$ | $R_2$ | $R_3$ | $R_5$ | Crystal form | M.p. (°C.) |
|---|---|---|---|---|---|---|---|
| 308 | 5 | H | $CH_3$ | H | $C_2H_5$ | Colorless needle-like crystals | 114–118 |
| 309 | 5 | H | $CH_3$ | $CH_3$ | $C_2H_5$ | Colorless needle-like crystals | 121.5–122.5 |
| 310 | 5 | $CH_3$ | H | H | $C_2H_5$ | Colorless needle-like crystals | 64.5–66.5 |
| 311 | 6 | H | H | H | $C_2H_5$ | Colorless needle-like crystals | 129–132.5 |
| 312 | 6 | H | $CH_3$ | $CH_3$ | $C_2H_5$ | Colorless needle-like crystals | 72–73.5 |
| 313 | 7 | H | H | H | $C_2H_5$ | Colorless needle-like crystals | 106–107 |
| 314 | 8 | H | $CH_3$ | H | $C_2H_5$ | Colorless needle-like crystals | 94–99 |
| 315 | 8 | H | $CH_3$ | $CH_3$ | $C_2H_5$ | Colorless needle-like crystals | 125–126.5 |

EXAMPLE 316

0.9 Gram of metallic sodium was dissolved in a solution of 4.8 g. of 5-hydroxycarbostyril in 100 ml. of ethylene glycol monomethyl ether. This solution was charged under stirring at 85° to 90° C. with 12 g. of cyclohexyl α-bromopropionate, and the resulting mixture was stirred at said temperature for 5 hours. After the reaction, the solvent was removed under reduced pressure, and the residue was dissolved in 100 ml. of chloroform. The resulting solution was washed with a 5% aqueous sodium carbonate solution and water in this order. The chloroform layer was dried with anhydrous sodium sulfate, and then the chloroform was removed under reduced pressure. Subsequently, the residue was crystallized with petroleum ether and then recrystallized from methanol to obtain 5.8 g. of 5-(1'-cyclohexyloxycarbonyl)ethoxycarbostyril in the form of colorless needle-like crystals, m.p. 176°–177° C.

EXAMPLE 317

0.9 Gram of metallic sodium was dissolved in a solution of 4.8 g. of 6-hydroxy-3,4-dihydrocarbostyril in 100 ml. of n-propanol. This solution was charged with 10 g. of n-propyl α-bromobutyrate and was stirred under reflux for 5 hours. After the reaction, the solvent was removed by distillation, and the residue was dissolved in 100 ml. of chloroform. The resulting solution was washed with a 5% aqueous sodium hydroxide solution and water in this order and dried with anhydrous sodium sulfate, and then the chloroform was removed under reduced pressure. Subsequently, the residue was crystallized with petroleum ether and then recrystallized from methanol to obtain 5.1 g. of 6-(1'-propoxycarbonyl)propoxy-3,4-dihydrocarbostyril in the form of colorless needle-like crystals, m.p. 100°–101° C.

EXAMPLE 318

3.2 Grams of 8-hydroxy-3,4-dihydrocarbostyril and 1.3 g. of sodium methylate were dissolved with heating in 50 ml. of methanol. The resulting solution was charged with 5.5 g. of methyl α-chloropropionate and then stirred under reflux for 5 hours. After the reaction, the solvent was removed by distillation, and the residue was dissolved in 50 ml. of chloroform. The resulting chloroform solution was washed with a 5% aqueous sodium hydroxide solution and water in this order and dried with anhydrous sodium sulfate, and then the chloroform was removed by distillation. Subsequently, the residue was crystallized with petroleum ether and then recrystallized from methanol to obtain 3.8 g. of 8-(1'-methoxycarbonyl)ethoxy-3,4-dihydrocarbostyril in the form of colorless plate-like crystals, m.p. 103°–104° C.

EXAMPLE 319

16 Grams of 7-hydroxy-3,4-dihydrocarbostyril and 9 g. of sodium ethylate was dissolved with heating in 200 ml. of ethanol. The resulting solution was charged with 25 g. of ethyl α-bromobutyrate and was refluxed for 8 hours. After the reaction, the solvent was removed under reduced pressure, and the residue was dissolved in 300 ml. of ethyl acetate. The resulting solution was washed with a 5% aqueous sodium hydroxide solution and water in this order and dried with anhydrous sodium sulfate, and then the ethyl acetate was removed by distillation. Subsequently, the residue was crystallized with petroleum ether and then recrystallized from ethanol to obtain 21 g. of 7-(1'-ethoxycarbonyl)propoxy-3,4-dihydrocarbostyril in the form of colorless plate-like crystals, m.p. 83°–85° C.

EXAMPLES 320–384

According to Example 316 such compounds as shown in Tables 18 and 19 were obtained.

Table 18

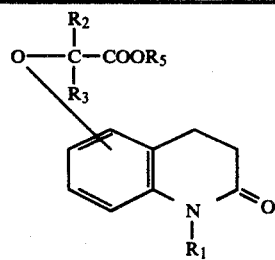

| Example No. | Portion of substituent | R₁ | R₂ | R₃ | R₅ | Properties Crystal form | M.p. (B.p.) °C. |
|---|---|---|---|---|---|---|---|
| 320 | 5 | H | H | H | $CH_3$ | Colorless needle-like crystals | 179–180 |
| 321 | 5 | H | H | H | $n$-$C_5H_{11}$ | " | 144–145 |
| 322 | 5 | H | H | H | | " | 163–164 |
| | | | | | $CH_2$—⟨Ph⟩ | | |
| 323 | 5 | H | H | H | ⟨C₆H₁₁⟩ | " | 162–163 |
| 324 | 5 | H | $CH_3$ | H | $CH_3$ | " | 137–138 |
| 325 | 5 | H | $CH_3$ | H | $n$-$C_3H_7$ | " | 111–112 |
| 326 | 5 | H | $CH_3$ | H | $i$-$C_3H_7$ | " | 134–135 |
| 327 | 5 | H | $CH_3$ | H | $n$-$C_4H_9$ | " | 103–104 |
| 328 | 5 | H | $CH_3$ | H | $n$-$C_5H_{11}$ | " | 102–103 |
| 329 | 5 | H | $CH_3$ | H | $i$-$C_5H_{11}$ | " | 107–108 |
| 330 | 5 | H | $CH_3$ | H | $CH_2$—⟨Ph⟩ | " | 132–134 |
| 331 | 5 | H | $CH_3$ | H | ⟨C₆H₁₁⟩ | " | 116–117 |
| 332 | 5 | H | $C_2H_5$ | H | $C_2H_5$ | " | 108–109 |
| 333 | 5 | H | $C_2H_5$ | H | $i$-$C_3H_7$ | " | 120–121 |
| 334 | 5 | H | $C_2H_5$ | H | $n$-$C_4H_9$ | " | 77–78 |
| 335 | 5 | H | $C_2H_5$ | H | $i$-$C_5H_{11}$ | " | 92–93 |
| 336 | 5 | H | $C_2H_5$ | H | $CH_2$—⟨Ph⟩ | " | 109–110 |
| 337 | 5 | H | $C_2H_5$ | H | ⟨C₆H₁₁⟩ | " | 123–124 |
| 338 | 5 | $CH_3$ | $CH_3$ | H | $C_2H_5$ | " | 44–45 |
| 339 | 5 | $CH_2$—⟨Ph⟩ | $CH_3$ | H | $C_2H_5$ | " | 75–78 |
| 340 | 5 | $CH_2$—$CH$=$CH_2$ | $CH_3$ | H | $C_2H_5$ | Colorless oil | (bp₀.₅ 157–158) |
| 341 | 5 | $CH_3$ | $C_2H_5$ | H | $C_2H_5$ | " | (bp₀.₆ 160–162) |
| 342 | 5 | $CH_2$—⟨Ph⟩ | $CH_3$ | H | $n$-$C_5H_{11}$ | " | (bp₀.₆ 211–213) |
| 343 | 6 | H | H | H | $CH_3$ | Colorless needle-like crystals | 155–156 |
| 344 | 6 | H | H | H | $n$-$C_4H_9$ | " | 118–119 |
| 345 | 6 | H | H | H | $i$-$C_5H_{11}$ | " | 77–78 |
| 346 | 6 | H | H | H | $CH_2$—⟨Ph⟩ | " | 151–152 |
| 347 | 6 | H | $CH_3$ | H | $CH_3$ | " | 139–140 |
| 348 | 6 | H | $CH_3$ | H | $i$-$C_3H_7$ | " | 125–126 |
| 349 | 6 | H | $CH_3$ | H | $n$-$C_4H_9$ | " | 102–103 |

Table 18-continued

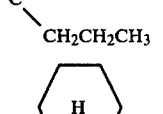

| Example No. | Portion of substituent | $R_1$ | $R_2$ | $R_3$ | $R_5$ | Properties Crystal form | M.p. (B.p.) °C. |
|---|---|---|---|---|---|---|---|
| 350 | 6 | H | $CH_3$ | H | $n-C_5H_7$ | " | 88–89 |
| 351 | 6 | H | $CH_3$ | H | $CH_2CH_3$ | Colorless plate-like crystals | 95–96 |
| | | | | | C | | |
| | | | | | $CH_2CH_2CH_3$ | | |
| 352 | 6 | H | $CH_3$ | H | 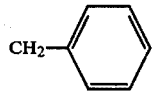 | Colorless needle-like crystals | 121–122 |
| 353 | 6 | H | $CH_3$ | H | 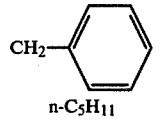 | Colorless plate-like crystals | 152–153 |
| 354 | 6 | H | $C_2H_5$ | H | $C_2H_5$ | " | 86–87 |
| 355 | 6 | H | $CH_3$ | H | $i-C_3H_7$ | Colorless needle-like crystals | 112–113 |
| 356 | 6 | $CH_3$ | $CH_3$ | H | $C_2H_5$ | Colorless oil | (bp$_{0.65}$ 170–172) |
| 357 | 6 | $CH_3$ | $C_2H_5$ | H | $C_2H_5$ | " | (bp$_{0.6}$ 160–162) |
| 358 | 6 | 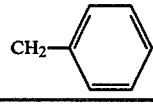 | $CH_3$ | H | $C_2H_5$ | " | (bp$_{0.8}$ 185–188) |
| 359 | 7 | H | $CH_3$ | H | $C_2H_5$ | Colorless needle-like crystals | 85–86 |
| 360 | 7 | H | $CH_3$ | $CH_3$ | 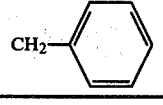 | " | 99–101 |
| 361 | 7 | H | $C_2H_5$ | H | $n-C_5H_{11}$ | " | 78–80 |
| 362 | 7 | $C_2H_5$ | $C_2H_5$ | H | $C_2H_5$ | Colorless oil | (bp$_2$ 188–190) |
| 363 | 8 | H | $C_2H_5$ | H | $C_2H_5$ | Colorless needle-like crystals | 71–72 |
| 364 | 8 | $CH_2$-Ph | $C_2H_5$ | H | $CH_2$-Ph | " | 99–101 |

Table 19

| Example No. | Position of substituent | $R_1$ | $R_2$ | $R_3$ | $R_5$ | Properties Crystal form | M.p. (B.p.) °C. |
|---|---|---|---|---|---|---|---|
| 365 | 5 | H | H | H | $CH_3$ | Colorless needle-like crystals | 256–258 |
| 366 | 5 | H | $CH_3$ | H | $CH_3$ | Colorless needle-like crystals | 196–198 |
| 367 | 5 | H | $CH_3$ | H | $n-C_3H_7$ | Colorless needle-like crystals | 153–154 |
| 368 | 5 | H | $CH_3$ | H | $i-C_3H_7$ | Colorless needle-like crystals | 182–183 |
| 369 | 5 | H | $CH_3$ | H | $n-C_5H_{11}$ | Colorless needle- | 151–152 |

Table 19-continued $$\text{O}-\underset{R_3}{\underset{|}{\overset{R_2}{\underset{|}{C}}}}-COOR_5$$

(structure: quinolinone with O-C(R2)(R3)-COOR5 substituent, N-R1, C=O)

| Example No. | Position of substituent | $R_1$ | $R_2$ | $R_3$ | $R_5$ | Crystal form | M.p. (B.p.) °C. |
|---|---|---|---|---|---|---|---|
| 370 | 5 | H | $CH_3$ | H | $CH_2$—⌬ | Colorless needle-like crystals | 182–183 |
| 371 | 5 | H | $C_2H_5$ | H | $C_2H_5$ | Colorless needle-like crystals | 147–149 |
| 372 | 5 | H | $C_2H_5$ | H | n-$C_4H_9$ | Colorless needle-like crystals | 144–145 |
| 373 | 5 | $CH_3$ | $CH_3$ | H | $C_2H_5$ | Colorless needle-like crystals | 69–71 |
| 374 | 5 | $C_2H_5$ | $CH_3$ | H | $C_2H_5$ | Colorless oil | (bp$_{0.8}$ 185–187) |
| 375 | 6 | H | H | H | $CH_3$ | Colorless needle-like crystals | 204–206 |
| 376 | 6 | H | $CH_3$ | H | $C_2H_5$ | Colorless needle-like crystals | 159–161 |
| 377 | 6 | H | $CH_3$ | H | n-$C_4H_9$ | Colorless needle-like crystals | 136–137 |
| 378 | 6 | H | $CH_3$ | H | ⌬H (cyclohexyl) | Colorless needle-like crystals | 162–163 |
| 379 | 6 | H | $C_2H_5$ | H | $C_2H_5$ | Colorless needle-like crystals | 129–130 |
| 380 | 6 | H | $C_2H_5$ | H | n-$C_3H_7$ | Colorless needle-like crystals | 120–122 |
| 381 | 7 | H | $CH_3$ | $CH_3$ | $C_2H_5$ | Colorless needle-like crystals | 137–140 |
| 382 | 7 | $C_2H_5$ | $C_2H_5$ | H | $C_2H_5$ | Colorless oil | (bp$_{0.4}$ 183–184) |
| 383 | 8 | H | H | H | $C_2H_5$ | Colorless needle-like crystals | 119–120 |
| 384 | 8 | H | $CH_3$ | $CH_3$ | $C_2H_5$ | Colorless needle-like crystals | 126–128 |

EXAMPLE 385

In 100 ml. of dimethyl sulfoxide were dissolved with stirring at 80° to 90° C. for 1 hour 19 g. of N-ethyl-5-hydroxy-3,4-dihydrocarbostyril, 10 g. of sodium ethylate and 2 g. of sodium iodide. The resulting solution was charged with 32 g. of ethyl γ-bromobutyrate and stirred at 100° to 110° C. for 10 hours. After the reaction, the reaction liquid was poured into 1.5 liters of saturated sodium chloride solution and then extracted with chloroform (300 ml.×4 times). The chloroform layer was washed with saturated sodium chloride solution, a 0.5 N-aqueous sodium hydroxide solution and water in this order, and then dried with anhydrous sodium sulfate. Subsequently, the chloroform layer was concentrated, and the concentrate was distilled under reduced pressure to obtain 21 g. of N-ethyl-5-(3'-ethoxycarbonyl)-propoxy-3,4-dihydrocarbostyril in the form of a colorless liquid, b.p. 0.9 189°–191° C.

EXAMPLE 386

To 100 ml. of ethanol were added 16 g. of 5-hydroxy-3,4-dihydrocarbostyril and 5.7 g. of sodium hydroxide, and the resulting mixture was concentrated to dryness. To the concentrate were then added 100 ml. of N,N-dimethylformamide, 2 g. of potassium iodide and 45 g. of propyl 5-bromovalerate, and the mixture was stirred at 100° to 110° C. for 10 hours. After the reaction, the reaction liquid was cooled and then poured into 1 liter of water to deposit crystals. The deposited crystals were recovered by filtration, and washed with a 0.5 N-aqueous sodium hydroxide solution and water in this order. Subsequently, the crystals were recrystallized from methanol to obtain 20 g. of 5-(4'-propoxycarbonyl)butoxy-3,4-dihydrocarbostyril in the form of colorless needle-like crystals, m.p. 94°–96° C.

EXAMPLE 387

To 100 ml. of ethanol were added 2.5 g. of metallic sodium and 16 g. of 6-hydroxy-3,4-dihydrocarbostyril, and the resulting mixture was concentrated to dryness. To the concentrate were then added 100 ml. of dimethyl sulfoxide and 2 g. of sodium iodide, and the mixture was stirred at room temperature for 1 hour to form a solution. This solution was reacted with 40 g. of ethyl 6-bromocaproate under stirring at 100° to 110° C. for 10 hours. After the reaction, the reaction liquid was poured into 1 liter of water to deposit crystals. The deposited crystals were recovered by filtration, washed with a 0.5 N-aqueous sodium hydroxide solution and water in this order, and then recrystallized from methanol to obtain 19 g. of 6-(6'-ethoxycarbonyl)hexyloxy-3,4-dihydrocarbostyril in the form of colorless needle-like crystals, m.p. 103°–105° C.

EXAMPLES 388–430

According to Example 385, such compounds as shown in Tables 20 and 21 were obtained.

Table 20

$$O(CH_2)_m\underset{R_3}{\overset{R_2}{C}}(CH_2)_nCOOR$$

(structure: 3,4-dihydrocarbostyril with N-$R_1$ and the above substituent on the benzene ring)

| Example No. | Position of substituent | $R_1$ | $(CH_2)_m\underset{R_3}{\overset{R_2}{C}}(CH_2)_n$ | $R_5$ | Crystal form | M.p. (B.p.) °C |
|---|---|---|---|---|---|---|
| 388 | 5 | H | $(CH_2)_3$ | $C_2H_5$ | Colorless needle-like crystals | 114–116 |
| 389 | 5 | H | $(CH_2)_3$ | $i$-$C_3H_7$ | Colorless needle-like crystals | 128–130 |
| 390 | 5 | H | $(CH_2)_3$ | $n$-$C_5H_{11}$ | Colorless needle-like crystals | 112–114 |
| 391 | 5 | H | $(CH_2)_3$ | cyclohexyl (H) | Colorless needle-like crystals | 122–124 |
| 392 | 5 | H | $(CH_2)_4$ | $C_2H_5$ | Colorless needle-like crystals | 118–120 |
| 393 | 5 | H | $(CH_2)_4$ | $i$-$C_5H_{11}$ | Colorless needle-like crystals | 96–98 |
| 394 | 5 | H | $(CH_2)_6$ | $C_2H_5$ | Colorless needle-like crystals | 98–100 |
| 395 | 5 | H | $(CH_2)_6$ | $n$-$C_4H_9$ | Colorless needle-like crystals | 79–81 |
| 396 | 5 | H | $(CH_2)_6$ | $CH_2C_6H_5$ | Colorless needle-like crystals | 84–86 |
| 397 | 5 | H | $(CH_2)_{10}$ | $C_2H_5$ | Colorless needle-like crystals | 97–99 |
| 398 | 5 | H | $CH_2\underset{\overset{\|}{CH_3}}{CH}CH_2$ | $C_2H_5$ | Colorless needle-like crystals | 95–97 |
| 399 | 5 | H | $CH_2-\underset{\overset{\|}{CH_3}}{CH}-CH_2$ | $n$-$C_4H_9$ | Colorless needle-like crystals | 84–85 |
| 400 | 5 | $C_2H_5$ | $(CH_2)_3$ | $n$-$C_5H_{11}$ | Colorless oil | (202–204/0.5) |
| 401 | 5 | $CH_2CH=CH_2$ | $(CH_2)_3$ | $i$-$C_3H_7$ | Colorless oil | (185–187/0.8) |
| 402 | 5 | $CH_2C_6H_5$ | $(CH_2)_6$ | $n$-$C_4H_9$ | Colorless needle-like crystals | 46–48 |
| 403 | 6 | H | $(CH_2)_2$ | $C_2H_5$ | Colorless needle-like crystals | 136–137 |
| 404 | 6 | H | $(CH_2)_3$ | $C_2H_5$ | Colorless needle-like crystals | 113–115 |
| 405 | 6 | H | $(CH_2)_3$ | $i$-$C_3H_7$ | Colorless needle-like crystals | 104–105 |
| 406 | 6 | H | $(CH_2)_3$ | $n$-$C_5H_{11}$ | Colorless needle-like crystals | 75–77 |
| 407 | 6 | H | $(CH_2)_4$ | $C_2H_5$ | Colorless needle-like crystals | 115–118 |
| 408 | 6 | H | $(CH_2)_4$ | $n$-$C_5H_{11}$ | Colorless needle-like crystals | 72–74 |
| 409 | 6 | H | $(CH_2)_6$ | $CH_2C_6H_5$ | Colorless needle-like crystals | 98–100 |
| 410 | 6 | H | $(CH_2)_{10}$ | $C_2H_5$ | Colorless needle-like crystals | 99–102 |
| 411 | 6 | H | $CH_2-\underset{\overset{\|}{CH_3}}{CH}-CH_2$ | $C_2H_5$ | Colorless needle-like crystals | 59–61 |
| 412 | 6 | H | $CH_2-\underset{\overset{\|}{CH_3}}{CH}-CH_2$ | $CH_2C_6H_5$ | Colorless needle-like crystals | 63–64 |
| 413 | 6 | H | $CH_2CH_2\underset{\overset{\|}{CH_3}}{CH}$ | $C_2H_5$ | Colorless oil | (206–208/0.6) |
| 414 | 6 | $CH_3$ | $(CH_2)_3$ | $C_2H_5$ | Colorless oil | (197–199/0.7) |

Table 20-continued

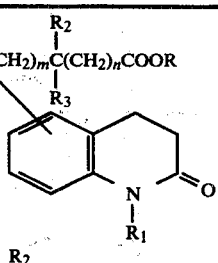

| Example No. | Position of substituent | $R_1$ | $(CH_2)_m\underset{R_3}{\overset{R_2}{C}}(CH_2)_n$ | $R_5$ | Crystal form | M.p. (B.p.) °C. |
|---|---|---|---|---|---|---|
| 415 | 7 | H | $(CH_2)_5$ | $C_2H_5$ | Colorless needle-like crystals | 71–72 |
| 416 | 7 | H | $(CH_2)_5$ | $n-C_4H_9$ | Colorless needle-like crystals | 82–84 |
| 417 | 8 | H | $(CH_2)_2$ | $n-C_3H_7$ | Colorless flake-like crystals | 86–87 |
| 418 | 8 | H | $(CH_2)_6$ | $n-C_3H_7$ | Colorless oil | (213–214/0.6) |

Table 21

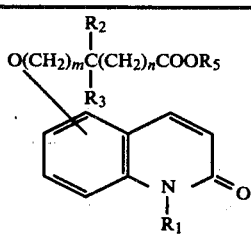

| Example No. | Position of substituent | $R_1$ | $(CH_2)_m\underset{R_3}{\overset{R_2}{C}}(CH_2)_n$ | $R_5$ | Crystal form | M.p. (B.p.) °C. |
|---|---|---|---|---|---|---|
| 419 | 5 | H | $(CH_2)_3$ | $C_2H_5$ | Colorless needle-like crystals | 171–173 |
| 420 | 5 | H | $(CH_2)_4$ | $n-C_3H_7$ | Colorless needle-like crystals | 130–131 |
| 421 | 5 | H | $(CH_2)_4$ | $i-C_5H_{11}$ | Colorless needle-like crystals | 134–136 |
| 422 | 5 | H | $(CH_2)_6$ | $C_2H_5$ | Colorless needle-like crystals | 138–139 |
| 423 | 5 | H | $(CH_2)_6$ | $CH_2C_6H_5$ | Colorless needle-like crystals | 111–112 |
| 424 | 5 | H | $\underset{CH_2CHCH_2}{\overset{CH_3}{|}}$ | $C_2H_5$ | Colorless needle-like crystals | 148–149 |
| 425 | 5 | $C_2H_5$ | $(CH_2)_3$ | $C_2H_5$ | Colorless oil | (191–193/0.55) |
| 426 | 6 | H | $(CH_2)_3$ | $C_2H_5$ | Colorless needle-like crystals | 130–132 |
| 427 | 6 | H | $(CH_2)_3$ | $n-C_5H_{11}$ | Colorless needle-like crystals | 96–97 |
| 428 | 6 | H | $(CH_2)_6$ | $C_2H_5$ | Colorless needle-like crystals | 129–130 |
| 429 | 6 | H | $(CH_2)_6$ | $CH_2C_6H_5$ | Colorless needle-like crystals | 141–143 |
| 430 | 6 | $CH_3$ | $(CH_2)_3$ | $C_2H_5$ | Colorless needle-like crystals | 89–90 |

REFERENTIAL EXAMPLE 6

To 200 ml. of ethanol were added 32 g. of 5-hydroxy-3,4-dihydrocarbostyril, 17 g. of sodium ethylate and 1 g. of potassium iodide, and the resulting mixture was refluxed with stirring for 1 hour to form a solution. Into this solution was dropped 56 g. of 1,6-dibromohexane, and the resulting mixture was refluxed with stirring for 12 hours. After the reaction, the reaction liquid was cooled to deposit crystals. The deposited crystals were recovered by filtration, washed with a 0.5 N-aqueous sodium hydroxide solution and water in this order, and then recrystallized from ethanol to obtain 40 g. of 5-(6'-bromo)hexyloxy-3,4-dihydrocarbostyril in the form of colorless needle-like crystals, m.p. 135°–136° C.

REFERENTIAL EXAMPLE 7

To 200 ml. of dimethyl sulfoxide were added 26 g. of 5-(6'-bromo)hexyloxy-3,4-dihydrocarbostyril and 5.5 g. of powdered sodium cyanide, and the resulting mixture was stirred at 100° to 110° C. for 5 hours. After cooling, the reaction liquid was poured into 1.5 liters of water to deposit crystals. The deposited crystals were recovered by filtration, washed with water and then recrystallized from ethyl acetate to obtain 21 g. of 5-(6'-cyano)hexyloxy-3,4-dihydrocarbostyril in the form of colorless amorphous solids, m.p. 169°–172° C.

REFERENTIAL EXAMPLE 8

To a solution of 3.3 g. of metallic sodium in 200 ml. of ethanol were added 19 g. of N-ethyl-5-hydroxy-3,4-dihydrocarbostyril and 2 g. of sodium iodide, and the resulting mixture was stirred at room temperature for 1 hour. Subsequently, the mixture was charged with 24 g. of 3-cyanopropyl bromide and then refluxed with stirring for 10 hours. After the reaction, the reaction liquid was concentrated, and the concentrate was dissolved in ethyl acetate. The ethyl acetate layer was washed with 0.5 N-aqueous sodium hydroxide solution and water in this order, and dried with anhydrous sodium sulfate. After removing the ethyl acetate by concentration, the residue was recrystallized from ligroin to obtain 15 g. of N-ethyl-5-(3'-cyano)propoxy-3,4-dihydrocarbostyril in the form of colorless amorphous solids, m.p. 74°–76° C.

REFERENTIAL EXAMPLE 9

A suspension of 11.4 g. of 5-hydroxy-3,4-dihydrocarbostyril in 37.1 g. of acrylonitrile was charged with 2 ml. of a 40% methanol solution of Triton B, and refluxed for 8.5 hours. The reaction liquid was cooled to deposit crystals, which were then recovered by filtration and recrystallized from methanol to obtain 6.5 g. of 5-(2'-cyanoethoxy)-3,4-dihydrocarbostyril in the form of colorless needle-like crystals, m.p. 217°–222.5° C.

EXAMPLE 431

In 100 ml of dimethylsulfoxide were dissolved with stirring at 80° to 90° C. for 1 hour 17 g. of 5-hydroxy-3,4-dihydrocarbostyril, 10 g. of sodium ethylate and 2 g. of sodium iodide. The resulting solution was charged with 31 g. of ethyl γ-bromocrotonate and stirred at 100° to 110° C. for 10 hours. After the reaction, the reaction liquid was poured into 1.5 liters of saturated sodium chloride solution and then extracted with chloroform. The chloroform layer was washed with saturated sodium chloride solution, a 0.5 N-aqueous sodium hydroxide solution and water in this order, and then dried with anhydrous sodium sulfate. Subsequently, the chloroform layer was concentrated, and then recrystallized from methanol to obtain 19 g. of 5-(3'-ethoxycarbonyl-2'-propenyloxy)-3,4-dihydrocarbostyril in the form of a colorless needle-like crystals, m.p. 152°–153° C.

EXAMPLE 432

To 100 ml. of ethanol were added 16 g. of 6-hydroxy-3,4-dihydrocarbostyril and 5.7 g. of sodium hydroxide, and the resulting mixture was concentrated to dryness. To the concentrate were then added 100 ml. of N,N-dimethylformamide, 2 g. of potassium iodide and 40 g. of ethyl γ-bromocrotonate, and the mixture was stirred at 100°–110° C. for 10 hours. After the reaction, the reaction liquid was cooled and then poured into 1 liter of water to deposit crystals. The deposited crystals were recovered by filtration, and washed with a 0.5 N-aqueous sodium hydroxide solution and water in this order. Subsequently, the crystals were recrystallized from methanol to obtain 18 g. of 6-(3'-ethoxycarbonyl-2')propenyloxy-3,4-dihydrocarbostyril in the form of colorless needle-like crystals, m.p. 151°–152° C.

EXAMPLE 433

According to Example 434, 6-(3'-ethoxycarbonyl-2'-propenyloxy)carbostyril in the form of colorless needle-like crystals, m.p. 213°–215° C. was obtained.

EXAMPLE 434

3.2 Grams of 5-hydroxy-N-methyl-2-oxyindole was dissolved in 15 ml. of dried dimethylformamide, then 960 mg. of 50% sodium hydride was added, and stirred at room temperature for 20 minutes. Into the thus obtained mixture, 4.3 g. of ethyl 3-bromobutyrate was added dropwise with stirring at the same temperature for 30 minutes, and further stirred at 70°–80° C. for 30 minutes. After the reaction, the reaction mixture was dissolved in 300 ml. of chloroform, and the chloroform solution was washed with water (100 ml.×5 times), then dried with anhydrous sodium sulfate. Subsequently, chloroform was distilled off and the thus obtained residue was recrystallized from a mixture of benzene-hexane to obtain 3.5 g. of 5-(3'-ethoxycarbonyl)propyloxy-N-methyl-2-oxyindole in the form of colorless prism-like crystals, m.p. 77.5°–79° C.

EXAMPLE 435

3.0 Grams of 5-hydroxyindole was dissolved in 15 ml of a 2:1 mixture of ethanol and dimethylformamide, then 1.0 g of sodium ethoxide was added and stirred at room temperature for 20 minutes. Into the thus obtained mixture, 4.0 g. of ethyl 3-bromobutyrate was added dropwise with stirring at the same temperature for 30 minutes, and further stirred at 70°–80° C. for 30 minutes. After the reaction, the reaction mixture was dissolved in 250 ml. of chloroform, and the chloroform solution was washed with water (100 ml.×5 times), then dried with anhydrous sodium sulfate. Subsequently, chloroform was distilled off and the thus obtained residue was recrystallized from isopropylether to obtain 3.0 g. of 5-(3'-ethoxycarbonyl)propyloxy-2-oxyindole in the form of colorless microplate-like crystals, m.p. 104°–106° C.

What is claimed is:

1. A compound of the formula

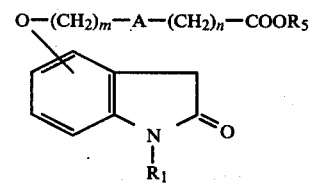

where $R_1$ is selected from the group consisting of hydrogen, $C_{1-4}$ alkyl, $C_{2-4}$ alkenyl, benzyl and phenethyl; A is —CH=CH— or

wherein $R_2$ or $R_3$ may be the same or different and are selected from the group consisting of hydrogen and $C_{1-4}$ alkyl; $R_5$ is selected from the group consisting of hydrogen, $C_{1-8}$ alkyl, cyclohexyl, benzyl and phenethyl and m and n each are zero or a positive integer with m+n being no more than 11.

2. A compound according to claim 1 wherein A is

3. A pharmaceutical composition for inhibiting platelet aggregation which comprises a compound as claimed in claim 1 and a pharmaceutically acceptable carrier.

4. A method for inhibiting platelet aggregation in the blood of a subject which comprises administering to the subject a pharmaceutical composition containing the compound of claim 1 and a pharmaceutically acceptable carrier in a dosage equivalent to about 0.1 mg. to about 100 mg. of said compound per day per kg. of weight of the subject.

5. 5-(3'-Ethoxycarbonyl)propoxy-2-oxyindole.

* * * * *